(12) United States Patent
Franano

(10) Patent No.: US 10,376,629 B2
(45) Date of Patent: *Aug. 13, 2019

(54) METHODS TO INCREASE THE OVERALL DIAMETER OF DONATING VEINS AND ARTERIES

(71) Applicant: FLOW FORWARD MEDICAL, INC., Olathe, KS (US)

(72) Inventor: F. Nicholas Franano, Olathe, KS (US)

(73) Assignee: Flow Forward Medical, Inc., Olathe, KS (US)

(*) Notice: Subject to any disclaimer, the term of this patent is extended or adjusted under 35 U.S.C. 154(b) by 160 days.

This patent is subject to a terminal disclaimer.

(21) Appl. No.: 15/402,050

(22) Filed: Jan. 9, 2017

(65) Prior Publication Data

US 2017/0112993 A1 Apr. 27, 2017

Related U.S. Application Data

(60) Division of application No. 14/239,251, filed as application No. PCT/US2012/050978 on Aug. 15, (Continued)

(51) Int. Cl.
*A61M 1/10* (2006.01)
*A61M 1/12* (2006.01)
(Continued)

(52) U.S. Cl.
CPC .......... *A61M 1/3655* (2013.01); *A61B 17/11* (2013.01); *A61B 90/39* (2016.02); *A61M 1/1008* (2014.02);
(Continued)

(58) Field of Classification Search
CPC .......... A61B 2017/00778; A61B 2018/00404; A61B 17/11; A61M 1/125; A61M 1/3655
See application file for complete search history.

(56) References Cited

U.S. PATENT DOCUMENTS

| 3,487,784 A | 1/1970 | Rafferty et al. |
| 3,771,910 A | 11/1973 | Laing |
| (Continued) | | |

FOREIGN PATENT DOCUMENTS

| CN | 1228140 A | 9/1999 |
| CN | 1278188 A | 12/2000 |
| (Continued) | | |

OTHER PUBLICATIONS

First Office Action from related Chinese Patent Application No. 201380053944.9, dated Jul. 5, 2016; 8 pgs.
(Continued)

*Primary Examiner* — Leslie R Deak
(74) *Attorney, Agent, or Firm* — Polsinelli PC

(57) ABSTRACT

A system and method for increasing the speed of blood and the wall shear stress in a peripheral artery or peripheral vein to a sufficient level and for a sufficient period of time to result in a persistent increase in the overall diameter and lumen diameter of the donating artery or donating vein is provided. The method includes systems and methods to effect the movement of blood at the desired rate and in the desired direction. The movement of blood is monitored and adjusted, as necessary, to maintain the desired blood speed and wall shear stress in the peripheral artery or vein in order to optimize the rate and extent of persistent diameter increase of the peripheral artery or peripheral vein.

73 Claims, 19 Drawing Sheets

Related U.S. Application Data 2012, now Pat. No. 9,539,380, and a continuation-in-part of application No. 13/030,054, filed on Feb. 17, 2011, now Pat. No. 9,155,827.

(60) Provisional application No. 61/561,859, filed on Nov. 19, 2011, provisional application No. 61/524,759, filed on Aug. 17, 2011, provisional application No. 61/305,508, filed on Feb. 17, 2010.

(51) Int. Cl.
    *A61M 1/14*     (2006.01)
    *A61M 1/36*     (2006.01)
    *A61B 17/11*     (2006.01)
    *A61M 25/01*     (2006.01)
    *A61B 90/00*     (2016.01)

(52) U.S. Cl.
CPC ........ *A61M 1/1029* (2014.02); *A61M 1/1086* (2013.01); *A61M 1/12* (2013.01); *A61M 1/14* (2013.01); *A61M 25/0194* (2013.01); *A61B 2017/1107* (2013.01); *A61B 2090/3966* (2016.02); *A61M 2205/3334* (2013.01); *A61M 2205/8206* (2013.01)

(56) References Cited

U.S. PATENT DOCUMENTS

| | | | |
|---|---|---|---|
| 3,864,055 | A | 2/1975 | Kletschka et al. |
| 4,457,673 | A | 7/1984 | Conley et al. |
| 4,507,048 | A | 3/1985 | Belenger et al. |
| 4,557,673 | A | 12/1985 | Chen et al. |
| 4,606,698 | A | 8/1986 | Clausen et al. |
| 4,665,896 | A | 5/1987 | LaForge et al. |
| 4,756,302 | A | 7/1988 | Portner et al. |
| 4,795,446 | A | 1/1989 | Fecht |
| 4,898,518 | A | 2/1990 | Hubbard et al. |
| 4,984,972 | A | 1/1991 | Clausen et al. |
| 4,994,017 | A | 2/1991 | Yozu |
| 5,006,104 | A | 4/1991 | Smith et al. |
| 5,017,103 | A | 5/1991 | Dahl |
| 5,162,102 | A | 11/1992 | Nogawa et al. |
| 5,178,603 | A | 1/1993 | Prince |
| 5,290,236 | A | 3/1994 | Mathewson |
| 5,300,015 | A | 4/1994 | Runge |
| 5,316,440 | A | 5/1994 | Kijima et al. |
| 5,324,177 | A | 6/1994 | Golding et al. |
| 5,360,317 | A | 11/1994 | Clausen et al. |
| 5,399,074 | A | 3/1995 | Nose et al. |
| 5,443,503 | A | 8/1995 | Yamane |
| 5,458,459 | A | 10/1995 | Hubbard et al. |
| 5,509,900 | A | 4/1996 | Kirkman |
| 5,509,908 | A | 4/1996 | Hillstead et al. |
| 5,527,159 | A | 6/1996 | Bozeman, Jr. et al. |
| D372,921 | S | 8/1996 | Ijiri et al. |
| 5,575,630 | A | 11/1996 | Nakazawa et al. |
| 5,588,812 | A | 12/1996 | Taylor et al. |
| 5,658,136 | A | 8/1997 | Mendler |
| 5,662,711 | A | 9/1997 | Douglas |
| 5,683,231 | A | 11/1997 | Nakazawa et al. |
| 5,707,218 | A | 1/1998 | Maher et al. |
| 5,713,730 | A | 2/1998 | Nose et al. |
| 5,746,575 | A | 5/1998 | Westphal et al. |
| 5,766,207 | A | 6/1998 | Potter et al. |
| 5,803,720 | A | 9/1998 | Ohara et al. |
| 5,851,174 | A | 12/1998 | Jarvik et al. |
| 5,858,003 | A | 1/1999 | Atala |
| 5,863,179 | A | 1/1999 | Westphal et al. |
| 5,890,883 | A | 4/1999 | Golding et al. |
| 5,894,011 | A | 4/1999 | Prosl et al. |
| 5,947,703 | A | 9/1999 | Nojiri et al. |
| 5,947,892 | A | 9/1999 | Benkowski et al. |
| 5,957,672 | A | 9/1999 | Aber |
| 5,989,206 | A | 11/1999 | Prosl et al. |
| 6,015,272 | A | 1/2000 | Antaki et al. |
| 6,050,975 | A | 4/2000 | Poirier |
| 6,093,001 | A | 7/2000 | Burgreen et al. |
| 6,110,139 | A | 8/2000 | Loubser |
| 6,116,862 | A | 9/2000 | Rau et al. |
| 6,152,704 | A | 11/2000 | Aboul-Hosn et al. |
| 6,162,017 | A | 12/2000 | Raible |
| 6,171,078 | B1 | 1/2001 | Schob |
| 6,183,220 | B1 | 2/2001 | Ohara et al. |
| 6,183,412 | B1 | 2/2001 | Benkowski et al. |
| 6,189,388 | B1 | 2/2001 | Cole et al. |
| 6,200,260 | B1 | 3/2001 | Bolling |
| 6,201,329 | B1 | 3/2001 | Chen |
| 6,217,541 | B1 | 4/2001 | Yu |
| 6,227,797 | B1 | 5/2001 | Watterson et al. |
| 6,227,817 | B1 | 5/2001 | Paden |
| 6,234,772 | B1 | 5/2001 | Wampler et al. |
| 6,244,835 | B1 | 6/2001 | Antaki et al. |
| 6,264,601 | B1 | 7/2001 | Jassawalla et al. |
| 6,299,575 | B1 | 10/2001 | Bolling |
| 6,346,071 | B1 | 2/2002 | Mussivand |
| 6,368,075 | B1 | 4/2002 | Fremerey |
| 6,439,845 | B1 | 8/2002 | Veres |
| 6,447,265 | B1 | 9/2002 | Antaki et al. |
| 6,447,266 | B2 | 9/2002 | Antaki et al. |
| 6,623,475 | B1 | 9/2003 | Siess |
| 6,652,447 | B2 | 11/2003 | Benkowski et al. |
| 6,688,861 | B2 | 2/2004 | Wampler |
| 6,692,318 | B2 | 2/2004 | McBride |
| 6,719,791 | B1 | 4/2004 | Nusser et al. |
| 6,742,999 | B1 | 6/2004 | Nusser et al. |
| 6,878,140 | B2 | 4/2005 | Barbut |
| 6,884,210 | B2 | 4/2005 | Nose et al. |
| 6,929,777 | B1 | 8/2005 | Litwak et al. |
| 6,969,345 | B2 | 11/2005 | Jassawalla et al. |
| 6,991,595 | B2 | 1/2006 | Burke et al. |
| 7,059,052 | B2 | 6/2006 | Okamura et al. |
| 7,138,776 | B1 | 11/2006 | Gauthier et al. |
| 7,160,242 | B2 | 1/2007 | Yanai |
| 7,172,550 | B2 | 2/2007 | Tsubouchi |
| 7,229,474 | B2 | 6/2007 | Hoffmann et al. |
| 7,357,425 | B2 | 4/2008 | Werth |
| 7,374,574 | B2 | 5/2008 | Nuesser et al. |
| 7,393,181 | B2 | 7/2008 | McBride et al. |
| 7,396,327 | B2 | 7/2008 | Morello |
| 7,467,929 | B2 | 12/2008 | Musser et al. |
| 7,476,077 | B2 | 1/2009 | Woodard et al. |
| 7,485,104 | B2 | 2/2009 | Kieval |
| 7,491,163 | B2 | 2/2009 | Viole et al. |
| 7,494,477 | B2 | 2/2009 | Rakhorst et al. |
| 7,572,217 | B1 | 8/2009 | Koenig et al. |
| 7,575,423 | B2 | 8/2009 | Wampler |
| 7,578,782 | B2 | 8/2009 | Miles et al. |
| 7,588,530 | B2 | 9/2009 | Heilman et al. |
| 7,614,997 | B2 | 11/2009 | Bolling |
| 7,614,998 | B2 | 11/2009 | Gross et al. |
| 7,699,586 | B2 | 4/2010 | LaRose et al. |
| 7,736,296 | B2 | 6/2010 | Siess et al. |
| 7,762,977 | B2 | 7/2010 | Porter et al. |
| 9,155,827 | B2 | 10/2015 | Franano |
| 9,539,380 | B2 * | 1/2017 | Franano .............. A61M 1/3655 |
| 9,555,174 | B2 | 1/2017 | Franano et al. |
| 9,662,431 | B2 | 5/2017 | Franano et al. |
| 2001/0001814 | A1 | 5/2001 | Estabrook et al. |
| 2001/0004435 | A1 | 6/2001 | Woodard et al. |
| 2002/0009242 | A1 | 1/2002 | Okamura et al. |
| 2002/0026944 | A1 | 3/2002 | Aboul-Hosn et al. |
| 2002/0076322 | A1 | 6/2002 | Maeda et al. |
| 2002/0161274 | A1 | 10/2002 | French et al. |
| 2002/0176798 | A1 | 11/2002 | Linker et al. |
| 2003/0163078 | A1 | 8/2003 | Fallen et al. |
| 2003/0233021 | A1 | 12/2003 | Nose et al. |
| 2003/0233144 | A1 | 12/2003 | Antaki et al. |
| 2004/0039243 | A1 | 2/2004 | Beamson et al. |
| 2004/0047737 | A1 | 3/2004 | Nose et al. |
| 2004/0133173 | A1 | 7/2004 | Edoga et al. |
| 2004/0171905 | A1 | 9/2004 | Yu et al. |
| 2004/0183305 | A1 | 9/2004 | Fisher |
| 2004/0186461 | A1 | 9/2004 | DiMatteo |

(56) References Cited

U.S. PATENT DOCUMENTS

| | | |
|---|---|---|
| 2004/0234397 A1 | 11/2004 | Wampler |
| 2005/0033107 A1 | 2/2005 | Tsubouchi |
| 2005/0038408 A1 | 2/2005 | von Segesser |
| 2005/0085684 A1 | 4/2005 | Rakhorst et al. |
| 2005/0113631 A1 | 5/2005 | Bolling et al. |
| 2005/0277964 A1 | 12/2005 | Brenneman et al. |
| 2006/0064159 A1 | 3/2006 | Porter et al. |
| 2006/0122552 A1 | 6/2006 | O'Mahony |
| 2006/0142633 A1 | 6/2006 | Lane et al. |
| 2006/0222533 A1 | 10/2006 | Reeves et al. |
| 2007/0135775 A1 | 6/2007 | Edoga et al. |
| 2007/0249986 A1 | 10/2007 | Smego |
| 2007/0253842 A1 | 11/2007 | Horvath et al. |
| 2008/0114339 A1 | 5/2008 | McBride et al. |
| 2008/0124231 A1 | 5/2008 | Yaegashi |
| 2008/0132748 A1 | 6/2008 | Shifflette |
| 2008/0240947 A1 | 10/2008 | Allaire et al. |
| 2008/0269880 A1 | 10/2008 | Jarvik |
| 2008/0281250 A1 | 11/2008 | Bergsneider et al. |
| 2009/0024072 A1 | 1/2009 | Criado et al. |
| 2009/0041595 A1 | 2/2009 | Garzaniti et al. |
| 2009/0156885 A1 | 6/2009 | Morello et al. |
| 2009/0209921 A1 | 8/2009 | Claude et al. |
| 2009/0234261 A1 | 9/2009 | Singh |
| 2010/0041939 A1 | 2/2010 | Siess |
| 2010/0204539 A1 | 8/2010 | Tansley et al. |
| 2010/0210990 A1 | 8/2010 | Lyons et al. |
| 2010/0222634 A1 | 9/2010 | Poirier |
| 2011/0002794 A1 | 1/2011 | Haefliger et al. |
| 2011/0196190 A1 | 8/2011 | Farnan et al. |
| 2011/0201990 A1 | 8/2011 | Franano |
| 2011/0243759 A1 | 10/2011 | Ozaki et al. |
| 2011/0257577 A1 | 10/2011 | Lane et al. |
| 2012/0065652 A1 | 3/2012 | Cully et al. |
| 2013/0338559 A1 | 12/2013 | Franano et al. |
| 2014/0296615 A1 | 10/2014 | Franano |
| 2014/0296767 A1 | 10/2014 | Franano |
| 2015/0157787 A1 | 6/2015 | Cully et al. |
| 2015/0209498 A1 | 7/2015 | Franano et al. |
| 2016/0030647 A1 | 2/2016 | Franano |
| 2016/0030648 A1 | 2/2016 | Franano |
| 2017/0258981 A1 | 9/2017 | Franano et al. |

FOREIGN PATENT DOCUMENTS

| | | |
|---|---|---|
| CN | 101024098 A | 8/2007 |
| CN | 101932837 A | 12/2010 |
| CN | 102844074 A | 12/2012 |
| EP | 1 825 872 A2 | 8/2007 |
| JP | 04-224760 A | 8/1992 |
| JP | 2696070 B2 | 9/1997 |
| JP | 2874060 B2 | 1/1999 |
| JP | 2000-102604 A | 4/2000 |
| JP | 3689567 B2 | 4/2000 |
| JP | 3085835 B2 | 7/2000 |
| JP | 2000-229125 A | 8/2000 |
| JP | 2005-058617 A | 3/2005 |
| JP | 4440499 B2 | 8/2005 |
| JP | 2007-516740 A | 6/2007 |
| JP | 2007-222670 A | 9/2007 |
| JP | 2011-502560 A | 1/2011 |
| RU | 2368811 C2 | 9/2009 |
| WO | 86/01395 A1 | 3/1986 |
| WO | 91/08783 A1 | 6/1991 |
| WO | 02/28314 A1 | 4/2002 |
| WO | 2004/043519 A1 | 5/2004 |
| WO | 2005/046779 A2 | 5/2005 |
| WO | 2008/136979 A1 | 11/2008 |
| WO | 2009/059371 A2 | 5/2009 |
| WO | 2009/064879 A2 | 5/2009 |
| WO | 2011/103356 A1 | 8/2011 |
| WO | 2013/025821 A2 | 2/2013 |
| WO | 2013/025826 A1 | 2/2013 |
| WO | 2014/028787 A2 | 2/2014 |
| WO | 2017/190155 A2 | 11/2017 |

OTHER PUBLICATIONS

Second Office Action and Search Report from related Chinese Patent Application No. 201380053944.9, dated May 3, 2017; 21 pgs.
Third Office Action from related Chinese Patent Application No. 201380053944.9, dated Jan. 3, 2018; 8 pgs.
Office Action from related Israel Patent Application No. 221503, dated May 15, 2015; 3 pgs.
Office Action from related Israel Patent Application No. 230992, dated Apr. 6, 2017; 3 pgs.
Office Action from related Israel Patent Application No. 230991, dated May 6, 2017; 3 pgs.
Office Action from related Japanese Patent Application No. 2012-554038, dated Nov. 4, 2014; 7 pgs.
Office Action from related Japanese Patent Application No. 2014-526181, dated Jun. 28, 2016; 6 pgs.
Office Action from related Japanese Patent Application No. 2014-526181, dated Jan. 31, 2017; 8 pgs.
Office Action from related Japanese Patent Application No. 2014-526178, dated Jun. 28, 2016; 5 pgs.
Office Action from related Japanese Patent Application No. 2015-527647, dated Jun. 27, 2017; 7 pgs.
Office Action from related Japanese Patent Application No. 2015-214417, dated Sep. 27, 2016; 7 pgs.
Office Action from related Japanese Patent Application No. 2015-214417, dated Aug. 22, 2017; 11 pgs.
Office Action from related Japanese Patent Application No. 2017-41461, dated Dec. 12, 2017; 3 pgs.
Office Action from related Korean Patent Application No. 10-2012-7022798, dated May 22, 2017; 2 pgs.
Office Action from related Russian Patent Application No. 2014109960, dated Aug. 3, 2016; 8 pgs.
Office Action from related Russian Patent Application No. 2014110029, dated Aug. 28, 2015; 3 pgs.
Office Action from related Russian Patent Application No. 2014110029, dated Dec. 14, 2016; 8 pgs.
Decision of Grant from related Russian Patent Application No. 2014110029, dated Nov. 24, 2017; 18 pgs.
Office Action from related Russian Patent Application No. 2015108946, dated May 27, 2015; 4 pgs.
Office Action from related Russian Patent Application No. 2015108946, dated Jul. 27, 2017; 5 pgs.
Office Action and Search Report from related Russian Patent Application No. 2015108946, dated Oct. 31, 2017; 14 pgs.
Office Action and Search Report from related Taiwan Patent Application No. 102129610, dated Jun. 14, 2017; 12 pgs.
Pries et al., "Remodeling of Blood Vessels: Responses of Diameter and Wall Thickness to Flemodynamic and Metabolic Stimuli," Hypertension, 2005, pp. 725-731, vol. 46.
Wiedeman, "Dimensions of Blood Vessels from Distributing Artery to Collecting Vein," Circulation Research, 1963, pp. 375-378, vol. 12.
Bennett et al., "Pump-induced haemolysis: a comparison of short-term ventricular assist devices," Perfusion, 2004, pp. 107-111, vol. 19, No. 2.
Choy et al., "A novel strategy for increasing wall thickness of coronary venules prior to retroperfusion," American Journal of Physiology—Heart and Circulatory Physiology, 2006, pp. H972-H978, vol. 291.
Supplementary European Search Report from related European Patent Application No. 11745274.8, dated Aug. 25, 2015; 9 pgs.
Office Action from related European Patent Application No. 11745274.8, dated May 9, 2016; 10 pgs.
Office Action from related European Patent Application No. 11745274.8, dated May 11, 2017; 4 pgs.
Supplementary European Search Report from related European Patent Application No. 12823591.8, dated Feb. 18, 2015; 7 pgs.
Office Action from related European Patent Application No. 12823591.8, dated Oct. 20, 2017; 11 pgs.
Extended European Search Report from related European Patent Application No. 12823758.3, dated Jun. 29, 2015; 10 pgs.

(56) References Cited

OTHER PUBLICATIONS

Supplementary European Search Report from related European Patent Application No. 13829746.0, dated May 9, 2016; 7 pgs.
Gujja et al., "Interventional Therapies for Heart Failure," SIS 2007 Yearbook, Chapter 13, pp. 65-75.
International Search Report and Written Opinion from related International Application No. PCT/US2011/025331, dated May 9, 2011; 22 pgs.
International Search Report and Written Opinion from related International Application No. PCT/US2012/050978, dated Feb. 8, 2013; 17 pgs.
International Search Report and Written Opinion from related International Application No. PCT/US2012/050983, dated Jan. 2, 2013; 14 pgs.
International Search Report and Written Opinion from related International Application No. PCT/US2013/055221, dated Feb. 3, 2014; 35 pgs.
International Search Report and Written Opinion from related International Application No. PCT/US2017/030476, dated Oct. 30, 2017; 55 pgs.
James et al., "Evaluation of Hemolysis in the VentrAssist Implantable Rotary Blood Pump," Artificial Organs, 2003, pp. 108-113, vol. 27, No. 1.
Jiang et al., "A novel vein graft model: adaptation to differential flow environments," American Journal of Physiology—Heart and Circulatory Physiology, 2004, pp. H240-H245, vol. 286.
Kawahito et al., "Hemolysis in Different Centrifugal Pumps," Artificial Organs, 1997, pp. 323-326, vol. 21, No. 4.
Kelly et al., "Characteristics of the response of the iliac artery to wall shear stress in the anaesthetized pig,"J. Physiol, 2007, pp. 731-743, vol. 582.2.
Moisiuk et al., "Permanent vascular access for haemodialysis: modern lines," Nephrology and Dialysis, 2002, 1, 4, pp. 14-24.
Office Action from related U.S. Appl. No. 13/030,054, dated Aug. 27, 2015; 15 pgs.
Office Action from related U.S. Appl. No. 13/030,054, dated Nov. 6, 2014; 32 pgs.
Office Action from related U.S. Appl. No. 13/030,054, dated Jun. 6, 2013; 28 pgs.
Office Action from related U.S. Appl. No. 13/030,054, dated Nov. 21, 2012; 19 pgs.
Office Action from related U.S. Appl. No. 13/968,070, dated Feb. 5, 2016; 18 pgs.
Office Action from related U.S. Appl. No. 13/968,070, dated Jul. 8, 2015; 14 pgs.
Office Action from related U.S. Appl. No. 14/239,251, dated Feb. 8, 2016; 13 pgs.
Office Action from related U.S. Appl. No. 14/421,767, dated Jan. 21, 2016; 34 pgs.
Office Action from related U.S. Appl. No. 14/239,248, dated Sep. 8, 2017; 16 pgs.
Office Action from related U.S. Appl. No. 15/607,198, dated Nov. 13, 2017; 8 pgs.
Office Action from related Australian Patent Application No. 2011217974, dated Jul. 4, 2014; 5 pgs.
Office Action from related Australian Patent Application No. 2012296568, dated Apr. 13, 2016; 3 pgs.
Office Action from related Australian Patent Application No. 2012296563, dated Apr. 14, 2016; 3 pgs.
Office Action from related Australian Patent Application No. 2013302455, dated Oct. 17, 2016; 4 pgs.
Office Action from related Australian Patent Application No. 2015258177, dated Apr. 6, 2017; 4 pgs.
Office Action from related Australian Patent Application No. 2017210640, dated Nov. 2, 2017; 3 pgs.
Office Action from related Canadian Patent Application No. 2,790,194, dated Feb. 8, 2017; 4 pgs.
First Office Action from related Chinese Patent Application No. 201180019380.8, dated Mar. 19, 2014; 8 pgs.
Second Office Action and Search Report from related Chinese Patent Application No. 201180019380.8, dated Oct. 23, 2014; 21 pgs.
Third Office Action from related Chinese Patent Application No. 201180019380.8, dated Jun. 26, 2015; 8 pgs.
Fourth Office Action from related Chinese Patent Application No. 201180019380.8, dated Dec. 22, 2015; 7 pgs.
First Office Action and Search Report from related Chinese Patent Application No. 2013103357853, dated Mar. 30, 2015; 23 pgs.
Second Office Action from related Chinese Patent Application No. 2013103357853, dated Feb. 2, 2016; 7 pgs.
Third Office Action from related Chinese Patent Application No. 201310335785.3, dated Sep. 19, 2016; 6 pgs.
First Office Action and Search Report from related Chinese Patent Application No. 201280050718.0, dated Nov. 4, 2015; 27 pgs.
Second Office Action and Search Report from related Chinese Patent Application No. 201280050718.0, dated Sep. 14, 2016; 24 pgs.
First Office Action and Search Report from related Chinese Patent Application No. 2012800507123, dated Apr. 5, 2016; 18 pgs.
Second Office Action from related Chinese Patent Application No. 201280050712.3, dated Mar. 14, 2017; 6 pgs.

\* cited by examiner

METHODS TO INCREASE THE OVERALL DIAMETER OF DONATING VEINS AND ARTERIES

CROSS REFERENCE TO RELATED APPLICATIONS

This application is a divisional of U.S. patent application Ser. No. 14/239,251, now U.S. Pat. No. 9,539,380, entitled "System and Method to Increase the Overall Diameter of Veins and Arteries", filed on Jun. 13, 2014 and issued on Jan. 10, 2017; which claims priority to PCT International Patent Application No. PCT/US2012/050978, entitled "System and Method to Increase the Overall Diameter of Veins and Arteries", filed Aug. 15, 2012, which claims priority to U.S. Provisional Application No. 61/561,859, entitled "System and Method to Increase the Overall Diameter of Veins and Arteries", filed Nov. 19, 2011, and also claims priority to U.S. Provisional Application No. 61/524,759, entitled "System and Method to Increase the Overall Diameter of Veins and Arteries", filed Aug. 17, 2011. U.S. patent application Ser. No. 14/239,251 is also a continuation-in-part of U.S. patent application Ser. No. 13/030,054, now U.S. Pat. No. 9,155,827, entitled "System and Method to Increase the Overall Diameter of Veins", filed Feb. 17, 2011 and issued on Oct. 13, 2015, which claims priority to U.S. Provisional Application No. 61/305,508, entitled "System and Method to Increase the Overall Diameter of Veins", filed Feb. 17, 2010. The present application is also related to PCT International Patent Application No. PCT/US2012/050983, entitled "Blood Pump Systems and Methods", filed Aug. 15, 2012, and is related to U.S. Provisional Application No. 61/524,761, entitled "System and Method to Increase the Overall Diameter of Veins", filed Aug. 17, 2011; and U.S. Provisional Application No. 61/564,671, entitled "Blood Pump Systems and Methods", filed Nov. 29, 2011, all of which are incorporated by reference in their entireties.

FIELD OF THE INVENTION

The present invention relates to systems and methods for persistently increasing the overall diameter and the lumen diameter of veins and arteries in humans. Specifically, the present invention relates to systems and methods that use a blood pump to increase the blood speed and wall shear stress (WSS) on the endothelium of peripheral veins and arteries for a sufficient period of time to result in a persistent increase in the overall diameter and lumen diameter of those veins and arteries.

BACKGROUND

Many patients with chronic kidney disease (CKD) eventually progress to end-stage renal disease (ESRD) and need renal replacement therapy to remove fluid and waste products from their bodies and sustain their lives. Most patients with ESRD needing renal replacement therapy receive hemodialysis, where blood is removed from the circulatory system, cleansed in a hemodialysis machine and then returned to the circulatory system. To facilitate hemodialysis, surgeons create discrete "vascular access sites" that can be used to remove and return blood rapidly from ESRD patients. While major advances have been made in hemodialysis machines themselves and other parts of the hemodialysis process, the creation of durable and reliable vascular access sites has seen only modest improvement and remains the Achilles' heel of renal replacement therapy. Failure to provide suitable vascular sites often results in sickness and death for ESRD patients and places a large burden on health care providers, payers, and public assistance programs worldwide.

Vascular access sites for hemodialysis generally come in three forms: arteriovenous fistulas (AVF), arteriovenous grafts (AVG), and catheters. Each type of access site is susceptible to high rates of failure and complications, as described below.

An AVF is constructed surgically by creating a direct connection between an artery and a vein. A functional AVF created at the wrist between the radial artery and the brachial vein is the longest-lasting and most desirable form of hemodialysis access, with a mean patency of about 3 years. The vein leading away from the connection is called the "outflow" vein. Persistent increases in the overall diameter and lumen diameter of the outflow vein are critical components for an AVF to "mature" and become usable. It is widely believed that the rapid flow of blood in the outflow vein created by the AVF and the WSS exerted on the endothelium of the vein is a major factor in bringing about persistent increases in the overall diameter and lumen diameter of the outflow vein. Unfortunately, approximately 80% of ESRD patients are not eligible for an AVF placement at the wrist, usually due to inadequate vein or artery diameters. For eligible patients where AVF placement is attempted, the site may not be usable without further intervention in about 50%-60% of cases, a problem known as "maturation failure." Small blood vessel diameter, especially small vein diameter, has been identified as a factor in AVF maturation failure. The rapid appearance of aggressive vein wall scarring known as "intimal hyperplasia" has also been identified as an important factor in AVF maturation failure. Some investigators have postulated that areas of relatively rapid or turbulent blood flow in the vein (with resultant high local WSS) are a major factor in causing vein wall scarring, while other investigators propose that this scarring is caused by areas of relatively slower or oscillating blood flow and relatively low or oscillating WSS. In response, attempts have been made to modulate flow patterns in AVF outflow veins in order to minimize AVF failure rates. Still other investigators have postulated that cyclic stretching of the vein caused by the entry of pulsatile arterial blood may also play a role in the stimulation of intimal hyperplasia and outflow vein obstruction in AVF. At the current time, no method exists which preserves the positive effects of elevated blood speed and WSS that cause persistent increases in the overall diameter and lumen diameter or arteries and veins, while eliminating the negative effects of vein wall scarring and obstruction. Not surprisingly, a patient newly diagnosed with ESRD and in need of hemodialysis has only a 50% chance of having a functional AVF six months after starting hemodialysis. Those patients without a functional AVF must undergo hemodialysis with more costly forms of vascular access and are at a greater risk of complications, sickness, and death.

A second type of vascular access site for hemodialysis is an arteriovenous graft (AVG). An AVG is constructed by placing a segment of synthetic conduit between an artery and vein. Typically, an AVG is constructed in the arm or the leg. A portion of the synthetic conduit is placed immediately under the skin and used for needle access. More patients are eligible for AVGs than AVFs, since veins not visible on the skin surface can be used for outflow, and the rate of early failure is much lower than that for AVFs. Unfortunately, AVGs have a mean primary patency of only about 4-6 months, because aggressive intimal hyperplasia and scarring develops rapidly in the wall of the outflow vein near the connection with the synthetic conduit, thus leading to stenosis and thrombosis. Similar to AVF failure, some investigators have postulated that the rapid and turbulent flow of blood in the outflow vein created by the AVG causes intimal hyperplasia and scarring in the wall of the outflow vein, while other investigators have proposed that this scarring is caused by areas of relatively slower or oscillating blood flow and relatively low or oscillating WSS. Still other investigators have postulated that cyclic stretching of the vein caused by the entry of pulsatile arterial blood into the outflow vein may also play a role in the formation of intimal hyperplasia and outflow vein obstruction in an AVG. Although AVGs are less desirable than AVFs, about 25% of patients dialyze with an AVG, mostly because they are not eligible to receive an AVF.

A third type of vascular access site is a catheter. Patients who are not able to get hemodialysis through an AVF or AVG can have a large catheter inserted in the neck, chest, or leg in order to receive hemodialysis. These catheters often become infected, thus placing the patient at high risk for sepsis and death. Patients with catheter sepsis usually require hospitalization, removal of the catheter, insertion of a temporary catheter, treatment with IV antibiotics, and then placement of a new catheter or other type of access site when the infection has cleared. Catheters are also susceptible to obstruction by thrombus and fibrin build-up around the tip. Hemodialysis catheters have a mean patency of about 6 months and are generally the least desirable form of hemodialysis access. Although catheters are less desirable than AVFs and AVGs, about 20% of patients dialyze with a catheter, mostly because they have not been able to receive a functional AVF or AVG, or are not eligible to receive an AVF or AVG.

The problem of hemodialysis access site failure has received more attention recently as the number of ESRD patients undergoing routine hemodialysis has increased worldwide. In 2004, the Centers for Medicare & Medicaid Services (CMS) announced a "Fistula First" initiative to increase the use of AVFs in providing hemodialysis access for patients with end-stage renal failure. This major initiative is a response to published Medicare data showing that patients who dialyze with an AVF have reduced morbidity and mortality compared to patients with an AVG or a catheter. Costs associated with AVF patients are substantially lower than the costs associated with AVG patients in the first year of dialysis, and in subsequent years. The cost savings of a dialyzing with an AVF are even greater when compared to dialyzing with a catheter.

To be eligible for an AVF, patients generally need to have a peripheral vein with an overall diameter of at least 2.5 mm and a peripheral artery with an overall diameter of at least 2.0 mm, with the understanding that different vascular surgeons will set different threshold levels. To be eligible for an AVG, patients generally need to have a peripheral vein with an overall diameter of at least 4 mm and a peripheral artery with an overall diameter of at least 3.0 mm, with the understanding that different vascular surgeons will set different threshold levels. Currently, there is no method for persistently increasing the overall diameter and lumen diameter of peripheral veins and arteries in ESRD patients who have inadequate initial vein or artery size prior to the creation of an AVF or AVG. Consequently, patients with veins or arteries that are too small to attempt an AVF or AVG must use less desirable forms of vascular access such as catheters. Similarly, there is currently no approved method for the treatment of AVF maturation failure, which falls disproportionately on patients with small vein and artery diameters, such as women and minorities. Thus, there is a desire for systems and methods for enlarging the overall diameter and lumen diameter of a vein or artery prior to the creation of AVF or AVG. A recent study demonstrated that ESRD patients who were forced to use less desirable forms of vascular access such as catheters had a substantially higher risk of becoming sick or dying when compared with patients who were able to use an AVF or AVG for hemodialysis.

There is also a need to persistently increase the vein or artery diameter for patients with atherosclerotic blockages of peripheral or coronary arteries in need of bypass grafting. Patients with peripheral artery disease (PAD), who have an obstruction to blood flow in the arteries of the legs, often suffer from claudication, skin ulceration, and tissue ischemia. Many of these patients may eventually require amputation of portions of the affected limb. In some PAD patients the obstruction can be relieved to an adequate degree by balloon angioplasty or the implantation of a vascular stent. In other patients, however, the obstruction is too severe for these types of minimally invasive therapies. Therefore, surgeons will often create bypass grafts that divert blood around the obstructed arteries and restore adequate blood flow to the affected extremity. However, many patients in need of a peripheral bypass graft cannot use their own veins as bypass conduits due to inadequate vein or artery diameter and are forced to use synthetic conduits made of materials such as expanded polytetrafluoroethylene (ePTFE, e.g. Gore-Tex) or polyethylene terephthalate (PET, e.g. Dacron). Studies have shown that using a patient's own veins as bypass conduits results in better long term patency than using synthetic bypass conduits made from materials such as PTFE, ePTFE, or Dacron. The use of a synthetic bypass conduit increases the risk of stenosis in the artery at the distal end of the graft and thrombosis of the entire conduit, thereby resulting in bypass graft failure and a recurrence or worsening of symptoms. Thus, there is a desire for systems and methods for increasing the overall diameter and lumen diameter of veins prior to the creation of bypass grafts for patients who are ineligible to use their own veins for the creation of a bypass graft due to inadequate vein diameter.

Patients with coronary artery disease (CAD) who have an obstruction to blood flow to their heart often suffer from chest pain, myocardial ischemia, and myocardial infarct and many of these patients eventually die from the disease. In some of these patients, the obstruction can be relieved to an adequate degree by balloon angioplasty or the implantation of a vascular stent. In many patients, however, the obstruction is too severe for these types of minimally invasive therapies. Therefore, surgeons will often create a bypass graft that diverts blood around the obstructed arteries and restores adequate blood flow to the affected regions of the heart, with the internal mammary arteries and the radial arteries as preferred conduits. However, some patients in need of coronary bypass grafts cannot use internal mammary or radial arteries due to inadequate artery diameter and must use peripheral veins. Studies have shown that using a patient's internal mammary and radial arteries as bypass conduits results in better long-term patency than using peripheral vein segments. The use of peripheral veins as bypass grafts increases the risk of stenosis in the graft and thrombosis of the entire conduit, resulting in bypass graft failure and a recurrence or worsening of symptoms. Thus, there is a desire for systems and methods for increasing the overall diameter and lumen diameter of arteries prior to the creation of coronary bypass grafts for patients who are ineligible to use their own arteries for the creation of a bypass graft due to inadequate artery diameter. Furthermore, systems and methods for increasing the overall diameter and lumen diameter of veins prior to the creation of coronary bypass grafts are also desired for patients with small peripheral vein diameters.

SUMMARY OF THE INVENTION

The present invention includes methods of using a blood pump to increase the overall diameter and the lumen diameter of peripheral veins and arteries. Systems and methods are described wherein either the mean wall shear stress or the peak wall shear stress exerted on the endothelium of a peripheral vein or artery is increased by pumping blood into the peripheral vein or artery at a sufficient rate and for a period of time sufficient to result in persistent increases in the overall diameter and lumen diameter of the peripheral vein or artery. The pump discharges the blood into the peripheral vein or artery preferably in a manner wherein the blood has reduced pulse pressure when compared with the pulse pressure of blood in a peripheral artery. Systems and methods are also described wherein the wall shear stress (WSS) exerted on the endothelium of the peripheral vein or artery is increased by pumping blood out of a peripheral vein or artery and to another location in the vascular system such as the right atrium at a sufficient rate and for a period of time sufficient to result in persistent increases in the overall diameter and lumen diameter of the peripheral vein or artery.

Studies have shown that baseline hemodynamic forces and changes in hemodynamic forces within veins and arteries play a vital role in determining the overall diameter and lumen diameter of those veins and arteries. For example, persistent increases in blood speed and WSS can lead to persistent increases in the overall diameter and lumen diameter of veins and arteries, where the amount of increase in the overall diameter and lumen diameter is dependent both on the level of increased blood speed and WSS and on the time that the blood speed and WSS are elevated. The elevated blood speed and WSS are sensed by endothelial cells, which trigger signaling mechanisms that result in the stimulation of vascular smooth muscle cells, the attraction of monocytes and macrophages, and the synthesis and release of proteases capable of degrading components of the extracellular matrix such as collagen and elastin. As such, the present invention relates to increasing blood speed and WSS for a period of time sufficient to result in vascular remodeling and persistent increases in the overall diameter and lumen diameter of veins and arteries, preferably for a period of time greater than seven days. The present invention also relates to methods of periodic manual or automatic adjustment of pump parameters to optimize the blood speed and WSS in the target artery or vein and to optimize the rate and extent of the persistent increases in the overall diameter and lumen diameter of veins and arteries.

Wall shear stress has been shown to be the key factor for causing persistent increases in the overall diameter and lumen diameter of veins and arteries in response to an increased blood flow. Assuming Hagen-Poiseuille blood flow in the vessel (i.e. a laminar flow with a fully developed parabolic velocity profile), then WSS is given by the equation:

$$WSS(Pa) = 4Q\mu/\pi R^3, \text{ where:}$$

Q=flow rate (m³/s)
μ=viscosity of blood (Pa/s)
R=radius of vessel (m)

The systems and methods described herein increase the WSS level in peripheral veins and arteries. Normal mean WSS for veins ranges between 0.076 Pa and 0.76 Pa. For persistent increases in the overall diameter and lumen diameter of veins, the systems and methods described herein increase the mean WSS level to a range between 0.76 Pa and 23 Pa, preferably to a range between 2.5 Pa and 10 Pa. Normal mean WSS for arteries ranges between 0.3 Pa and 1.5 Pa. For persistent increases in the overall diameter and lumen diameter of arteries, the systems and methods described herein increase the mean WSS level to a range between 1.5 Pa and 23 Pa, preferably to a range between 2.5 Pa and 10 Pa. Preferably, the mean WSS is increased for between 1 day and 84 days (or longer) to induce persistent increases in the overall diameter and lumen diameter of peripheral veins and arteries that were initially ineligible or suboptimal for use as a hemodialysis access site or bypass graft due to a small vein and artery diameter become usable or more optimal. This can also be accomplished by intermittently increasing mean WSS during the treatment period, with intervening periods of normal mean WSS.

The systems and methods described herein also increase the speed and/or velocity of blood in peripheral veins and arteries. At rest, the mean speed of blood in the cephalic vein in humans is generally range between 5 and 9 cm/s (0.05 and 0.09 m/s). For the systems and methods described herein, the mean speed of blood in the peripheral vein is increased to a range between 10 cm/s and 120 cm/s (0.1 and 1.2 m/s), preferably to a range between 25 cm/s and 100 cm/s (0.25 and 1.0 m/s), depending on the initial diameter of vein, the desired post-treatment diameter of the vein, and the length of time of treatment (with elevated WSS) is planned.

At rest, the mean speed of blood in the brachial artery generally ranges between 10 and 15 cm/s (0.1 and 0.15 m/s). For the systems and methods described herein, the mean speed of blood in the peripheral artery is increased to a range between 10 cm/s and 120 cm/s (0.1 and 1.2 m/s), and preferably to a range between 25 cm/s and 100 cm/s (0.25 and 1.0 m/s) depending on the initial diameter of the artery, the desired post-treatment diameter of the artery, and the length of time of treatment (with elevated WSS) is planned.

Preferably, the mean blood speed is increased for between 1 day and 84 days (or longer), or preferably, between 7 and 42 days, to induce persistent increases in the overall diameter and lumen diameter of the peripheral veins and arteries such that veins and arteries that were initially ineligible or suboptimal for use as a hemodialysis access site or bypass graft due to a small vessel diameter become usable or more optimal. This can also be accomplished by intermittently increasing mean blood speed during the treatment period, with intervening periods of normal mean blood speed.

A method of increasing the lumen diameter and overall diameter of a peripheral vein or peripheral artery in a patient is set forth herein. The method comprises performing a first procedure to access an artery, vein, or the right atrium (the donating vessel) and a peripheral vein or artery (the accepting vessel) and "fluidly connecting" (i.e. joining the two vessels lumen to lumen to permit fluid communication therebetween) the donating vessel to the accepting vessel with a pump system. The pump system is then activated to actively move blood from the donating vessel to the accepting vessel. The method also includes monitoring the blood pumping process for a period of time. The method further includes adjusting the speed of the pump, the speed of the blood and/or velocity of the blood being pumped where a particular direction or vector of blood flow is desired (such as in an anterograde or retrograde direction), the mean WSS or the peak WSS on the endothelium of the accepting vessel, and monitoring the pumping process again. After a period of time has elapsed to result in a persistent increase in the overall diameter and lumen diameter of the accepting vessel, the diameter of the accepting vessel is measured to determine if an adequate persistent increase in the overall diameter and lumen diameter of the accepting vessel has been achieved. The blood speed and/or velocity and the WSS are measured and the pumping process is adjusted again, as necessary. When an adequate amount of persistent increase in the overall diameter and lumen diameter of the accepting vessel has been achieved, a second surgery is performed to remove the pump. A hemodialysis access site (such as an AVF or AVG) or bypass graft can be created at the time of pump removal, or a later time, using at least a portion of the persistently enlarged accepting vessel.

A method of increasing the lumen diameter and overall diameter of a peripheral vein or peripheral artery in a patient is also set forth herein. The method comprises using a blood pump system to fluidly connect a peripheral artery or vein (the donating vessel) and another location in the venous system (the accepting location) and then activating the blood pump system to actively move blood from the donating vessel to the accepting location, optionally using one or more blood conduits. The method also includes monitoring the blood pumping process for a period of time. The method further includes adjusting the speed of the pump, the speed of the blood being pumped, or the mean WSS or the peak WSS on the endothelium of the donating vessel and monitoring the pumping process again. After a period of time has elapsed to result in a persistent increases in the overall diameter and lumen diameter of the donating vessel, the diameter of the donating vessel is measured to determine if an adequate persistent increase in the overall diameter and lumen diameter of the donating vessel has been achieved, the blood speed, the WSS are measured, and the pumping process is adjusted again, as necessary. When an adequate amount of persistent increase in the overall diameter and lumen diameter of the donating vessel has been achieved, a second surgery is performed to remove the pump. A hemodialysis access site (such as an AVF or AVG) or bypass graft can be created at the time of pump removal, or a later time, using at least a portion of the persistently enlarged donating vessel.

In one embodiment, a surgical procedure is performed to expose segments of two veins. One end of a first synthetic conduit is fluidly connected to the vein where blood is to be removed (the donating vein). The other end of the first synthetic conduit is fluidly connected to the inflow port of a pump. One end of a second synthetic conduit is fluidly connected to the vein where blood is to be moved (the accepting vein). The other end of the second synthetic conduit is fluidly connected to the outflow port of the same pump. Deoxygenated blood is pumped from the donating vein to the accepting vein until the overall diameter and lumen diameter of the accepting vein has persistently increased to the desired amount. The term "persistent increase" or "persistent dilation" when used to describe dilation or an increase in the overall diameter and lumen diameter of an artery or vein, is used herein to mean that even if a pump is turned off an increase in overall diameter or lumen diameter of a vessel can still be demonstrated, when compared to the overall diameter or lumen diameter of the vessel prior to the period of blood pumping. That is, the overall diameter or lumen diameter of the vessel has become larger independent of the pressure generated by the pump. Once the desired amount of persistent increase in the overall diameter and lumen diameter of the accepting vein has occurred, a second surgical procedure is performed to remove the pump and synthetic conduits. A hemodialysis access site (such as an AVF or AVG) or bypass graft can be created at the time of pump removal, or a later time, using at least a portion of the persistently enlarged accepting vein. In this embodiment, the pump port may be fluidly connected directly to the donating vein or the accepting vein without using an interposed synthetic conduit. In a variation of this embodiment, the accepting vein may be located in one body location, such as the cephalic vein in an arm and the donating vein may be in another location, such as the femoral vein in a leg. In this instance, the two ends of the pump-conduit assembly will be located within the body and a bridging portion of the pump-conduit assembly may be extracorporeal (outside the body, e.g. worn under the clothing) or implanted (e.g. tunneled in the subcutaneous tissues). Furthermore, in certain instances, the donating vessel may be more peripheral in relative body location than the accepting vein.

In another embodiment, a method comprises a surgical procedure that is performed to expose a segment of a peripheral artery and a segment of a peripheral vein. One end of a first synthetic conduit is fluidly connected to the peripheral artery. The other end of the first synthetic conduit is fluidly connected to the inflow port of a pump. One end of a second synthetic conduit is fluidly connected to the peripheral vein. The other end of the second synthetic conduit is fluidly connected to the outflow port of the same pump. Pumping oxygenated blood from the peripheral artery to the peripheral vein is performed until the overall diameter and lumen diameter of the vein or artery has persistently increased to the desired level. Once the desired amount of persistent increase in the overall diameter and lumen diameter of the vein or artery has occurred, a second surgical procedure is performed to remove the pump and synthetic conduits. A hemodialysis access site (such as an AVF or AVG) or bypass graft can be created at the time of pump removal, or a later time, using at least a portion of the persistently enlarged accepting vein or donating artery, or both. A variation of this embodiment is provided wherein the pump port may be fluidly connected directly to the artery or vein without using an interposed synthetic conduit.

In another embodiment, a method comprises a surgical procedure that is performed to expose a segment of a peripheral vein. One end of a first synthetic conduit is fluidly connected to the peripheral vein (the donating vessel), with the other end of the first synthetic conduit fluidly connected to the inflow port of a pump. One end of a second synthetic conduit is fluidly connected to the superior vena cava (the accepting location), with the other end of the second synthetic conduit fluidly connected to the outflow port of the same pump. Pumping deoxygenated blood from the donating peripheral vein to the superior vena cava is performed until the overall diameter and lumen diameter of the donating peripheral vein has persistently increased to the desired level. Once the desired amount of persistent increase in the overall diameter and lumen diameter has occurred in the donating peripheral vein, a second surgical procedure is performed to remove the pump and synthetic conduits. A hemodialysis access site (such as an AVF or AVG) or bypass graft can be created at the time of pump removal, or a later time, using at least a portion of the persistently enlarged peripheral donating vein. A variation of this embodiment is provided wherein at least one venous valve is rendered incompetent between 1) the connection of the first synthetic conduit and the peripheral donating vein and 2) the right atrium, to allow for retrograde flow into the peripheral donating vein.

In another embodiment, a method comprises a surgical procedure that is performed to expose a segment of a peripheral artery. One end of a first synthetic conduit is fluidly connected to the peripheral artery (the donating vessel), with the other end of the first synthetic conduit fluidly connected to the inflow port of a pump. One end of a second synthetic conduit is fluidly connected to the superior vena cava (the accepting location) with the other end of the second synthetic conduit fluidly connected to the outflow port of the same pump. Pumping oxygenated blood from the peripheral artery to the superior vena cava is performed until the overall diameter and lumen diameter of the peripheral donating artery has persistently increased to the desired level. Once the desired amount of persistent increase in the overall diameter and lumen diameter of the peripheral donating artery has occurred, a second surgical procedure is performed to remove the pump and synthetic conduits. A hemodialysis access site (such as an AVF or AVG) or bypass graft can be created at the time of pump removal, or a later time, using at least a portion of the persistently enlarged peripheral donating artery. A variation of this embodiment is provided wherein a synthetic conduit is used to directly fluidly connect the donating vessel (such as a peripheral artery) and the accepting location (such as the superior vena cava or the right atrium) wherein blood flows passively from a high-pressure donating artery to a low-pressure accepting location without a pump. In this embodiment, increased blood speed and WSS in the donating artery results from the shunt of blood from the high-pressure donating artery to the low-pressure accepting location and when maintained for a sufficient amount of time, results in a persistent increase in the overall diameter and lumen diameter of the donating artery. This embodiment is distinct from existing peripheral artery to right atrium grafts for hemodialysis, in that the system and method are configured to induce a persistent increase in the overall diameter and lumen diameter of the donating artery and are not configured for routine needle punctures or routine vascular access for hemodialysis. For example, the synthetic conduit in this embodiment has a shorter segment of synthetic material, such as PTFE, ePTFE, or Dacron, which allows for anastomosis to a peripheral artery but is not useful or optimal for routine needle punctures to gain vascular access for hemodialysis.

In another embodiment, a pair of specialized catheters is inserted into the venous system. The first end of one catheter (hereafter the "inflow conduit") is attached to the inflow port of a pump while the first end of the other catheter (hereafter the "outflow conduit") is attached to the outflow port of the pump. Optionally, a portion of the two catheters can be joined together to form a double lumen catheter. In one embodiment, each of the conduits have an individual length of between 2 cm and 110 cm and a combined length between 4 cm and 220 cm, and may be trimmed to a desired length by a surgeon or other physician, including during implantation of the pump system. The conduits each have an inner diameter between 2 mm and 10 mm, and preferably 4 mm. The conduits may be formed at least in part from polyurethane (such as Pellethane® or Carbothane ®), polyvinyl chloride, polyethylene, silicone elastomer, polytetrafluoroethylene (PTFE), expanded polytetrafluoroethylene (ePTFE), polyethylene terephthalate (PET, e.g. Dacron), and combinations thereof. The catheters are configured for insertion into the lumen of the venous system. After insertion, the tip of the second end of the inflow conduit is positioned anywhere in the venous system where a sufficient amount of blood can be drawn into the inflow catheter (the "donating location," such as the right atrium, superior vena cava, subclavian vein, or brachiocephalic vein). After insertion, the tip of the second end of the outflow conduit is positioned in a segment of peripheral vein (the "accepting vein") where blood can be delivered by the outflow conduit (such as cephalic vein near the wrist or the basilic vein near the elbow). The pump then draws deoxygenated blood into the lumen of the inflow conduit from the donating location and discharges the blood from the outflow conduit and into the lumen of the accepting vein. In this embodiment, the pump and a portion of the inflow conduit and outflow conduit may remain external to the patient. The pump is operated until the desired amount of persistent increase in the overall diameter and lumen diameter has occurred in the accepting vein, whereupon the pump and conduits are removed. A hemodialysis access site (such as an AVF or AVG) or bypass graft can be created at the time of pump removal, or a later time, using at least a portion of the persistently enlarged accepting vein.

A system for increasing the blood speed, the mean WSS and/or the peak WSS in a vein by delivery of deoxygenated blood from a donating vein or right atrium to an accepting vein in a patient is provided that comprises two synthetic conduits, each with two ends, a blood pump, a control unit, and a power source. This system may also contain one or more sensor units. In one embodiment of the system, the synthetic conduits and pump, collectively known as the "pump-conduit assembly" is configured to remove deoxygenated blood from a donating vein or the right atrium and pump that blood into a peripheral accepting vein. The pump-conduit assembly is configured to pump deoxygenated blood. In another embodiment of the system, the pump-conduit assembly is configured to remove oxygenated blood from a peripheral donating artery and pump the blood into a peripheral accepting vein. The blood is pumped in a manner that increases the blood speed in both the artery and vein and increases WSS exerted on the endothelium of the artery and the vein to a level and for a period of time sufficient to cause a persistent increase in the overall diameter and lumen diameter of the peripheral artery and the vein. Preferably, the blood being pumped into peripheral vein has low pulsatility, for example lower pulsatility than the blood in a peripheral artery. A variation of this embodiment is provided whereby the pump is fluidly connected directly to the artery or vein (or both) without using an interposed synthetic conduit.

The pump includes an inlet and an outlet. The pump is configured to deliver deoxygenated or oxygenated blood to the peripheral vein in a manner that increases the speed of the blood in the vein and increases the WSS exerted on the endothelium in the vein to cause a persistent increase in the overall diameter and the lumen diameter of the peripheral accepting vein, peripheral donating artery, or peripheral donating vein, depending on the particular embodiment and manner in which the blood pump system is connected to the vascular system and operated. The blood pump may be implanted in the patient, may remain external to the patient, or may have implanted and external portions. All or some of the synthetic conduits may be implanted in the patient, may be implanted subcutaneously, or may be implanted within the lumen of the venous or arterial system, or any combination thereof. The implanted portions of pump-conduit assembly may be monitored and adjusted periodically, for example, every second, minute, hour, day, or multiple days.

The invention includes methods of increasing the blood speed in a peripheral vein or peripheral artery and increasing the WSS exerted on the endothelium of a peripheral vein or peripheral artery of a human patient in need of a hemodialysis access site or a bypass graft, or other vascular surgery procedure or clinical situation where a larger peripheral artery or vein is beneficial. A device designed to augment arterial blood flow for the treatment of heart failure would be useful for this purpose. In addition, any pump that can increase blood speed and increase the WSS exerted on an accepting vessel may be used. In certain embodiments, a ventricular assist device (VAD) which is optimized for low blood flows would be capable of pumping blood from a donating artery or vein to a peripheral vein to induce a persistent increase in overall diameter and lumen diameter of a peripheral accepting vein and could be repurposed to increase blood speed and WSS in peripheral accepting veins to a level and for a time sufficient to cause a persistent increase in overall diameter and lumen diameter of these peripheral arteries and veins. In other embodiments, a VAD, which is capable of producing low blood flows, would be capable of pumping blood from a donating vessel (artery or vein) to an accepting location and could be repurposed to increase blood speed and WSS in peripheral donating arteries and peripheral donating veins to a level and for a time sufficient to cause a persistent increase in overall diameter and lumen diameter of those peripheral arteries and veins. In one embodiment, a pediatric VAD such as the PediPump may be used. In another embodiment a miniature VAD designed to treat moderate heart failure in adults (such as the Synergy pump by Circulite) may be used. Other devices, including a left ventricular assist device (LVAD) or a right ventricular assist device (RVAD) that are capable of low blood flows may also be used. In other embodiments, an adjustable centrifugal or rotary blood pump, whose operation is capable of real-time adjustments, may be used to draw blood from a donating vessel and pump the blood to an accepting vessel.

The method comprises fluidly connecting the low-flow VAD, a derivative thereof, or a similar type device to a donating vessel, removing blood from the donating vessel, and pumping it into the peripheral accepting vein at a sufficient flow rate and for a sufficient amount of time to cause a desired amount of persistent increase in the overall diameter and the lumen diameter of the peripheral vein. The method also comprises fluidly connecting the low-flow VAD, a derivative thereof, or a similar type device to a donating vessel (artery or vein), removing blood from the donating vessel, and pumping it into an accepting location at a sufficient flow rate and for a sufficient amount of time to cause a desired amount of persistent increase in the overall diameter and the lumen diameter of the donating vessel. The blood pump may be implanted into the patient or it may remain external to the patient. When the pump is external to the patient, it may be affixed to the patient for continuous pumping. Alternatively, the pump may be configured to detach from the donating and accepting vessels of the patient for periodic and/or intermittent pumping sessions.

The lumen diameter of peripheral accepting veins, peripheral donating arteries, and peripheral donating veins can be monitored while blood is being pumped using conventional methods such as visualization with ultrasound, diagnostic angiography, or magnetic resonance imaging, or other methods. A pump-conduit assembly or pump-catheter assembly may incorporate features that facilitate diagnostic angiography, such as radiopaque markers, that identify sites that can be accessed with a needle or syringe for injection of contrast into the assembly that will subsequently flow into the accepting peripheral vein and make it visible during fluoroscopy using both conventional and digital subtraction angiography. Similarly, a blood pump system may incorporate features that facilitate ultrasound or MRI, such as making MRI-compatible blood pump systems. In other embodiments, the blood pump system may incorporate a control system having one or more sensors in communication with the blood pump or conduits to measure at least one of a blood speed, a rate of blood flow, a resistance to blood flow into a peripheral blood vessel, a blood pressure, a pulsatility index, and combinations thereof "Pulsatility" and "pulsatility index", as used herein refer to a measure of the variability of blood speed in a vessel, equal to the difference between the peak systolic and minimum diastolic velocities divided by the mean velocities during the cardiac cycle.

When a portion of a pump-conduit assembly or pump-catheter assembly is located external to the body, an antimicrobial coating can be incorporated onto the external surface to at least the portion of the device including conduits, catheters, pumps, leads, or any combination thereof, especially portions that connect implanted and external components. For example, when a controller and/or power source is strapped to the arm or wrist, attached to a belt, or carried in a bag or pack, then the antimicrobial coating can be incorporated on the surface of materials that enters the patient's body, such as synthetic conduits, catheters, or pump leads. In another embodiment, a cuff may be applied to the portions of the device that connect the implanted and external components. The cuff may reduce the risk of infection by facilitating tissue incorporation and may reduce the incidence of wound opening by the reducing the mobility of the connection point. In another embodiment, a coating that reduces the accumulation of thrombus (such as an anti-thrombotic coating) can be incorporated onto the internal blood-contacting surfaces of the pump-conduit assembly and pump-catheter assembly. The anti-thrombotic coating can be incorporated into the conduits, catheters, pumps, or any combination thereof. In other embodiments a coating that increases lubriciousness can be added, such as to conduits or leads, in order to reduce friction during insertion or subcutaneous tunneling, and facilitate the insertion or subcutaneous tunneling process.

In various embodiments, the invention includes systems and methods for increasing an overall diameter of a peripheral artery of a patient by removing oxygenated blood from the peripheral artery and pumping the oxygenated blood into the right atrium at a flow rate and for a time period sufficient to result in a persistent increase in the overall diameter of the peripheral artery. The blood may be moved from the peripheral artery to the right atrium with or without the use of a pump. Similarly, in another embodiment, the invention includes systems and methods for increasing the overall diameter of a peripheral vein of a patient by removing deoxygenated blood from the peripheral vein and pumping the deoxygenated blood into the right atrium at a flow rate and for a time period sufficient to result in a persistent increase in the overall diameter of the peripheral vein.

Arteries and veins that experience sustained increases in blood speed and WSS can increase their overall and lumen diameter, and can also increase their overall length. As arteries and veins have branches that are somewhat fixed, they respond to the increase in overall length by increasing tortuosity in between the regions of branch point fixation. In certain clinical situations, an increase in vessel length may be desirable and thus become a primary motivation for implanting, configuring, and operating an embodiment of the pump-conduit assembly. In this embodiment, the vessel can be removed after experiencing an increase in length and used in another location (such as for the creation of bypass graft where a shorter segment would not be optimal) or the vessel can be freed from the branch point fixation by transecting and ligating the branch points. The vessel may then be reconfigured in situ to take advantage of the increased length (such as for creating a basilic vein transposition hemodialysis access site where a shorter segment would not be optimal).

These and other objects, features, aspects and advantages of the present invention will become apparent to those skilled in the art from the following detailed description, which, taken in conjunction with the annexed drawings, discloses preferred embodiments of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Figure 1A:
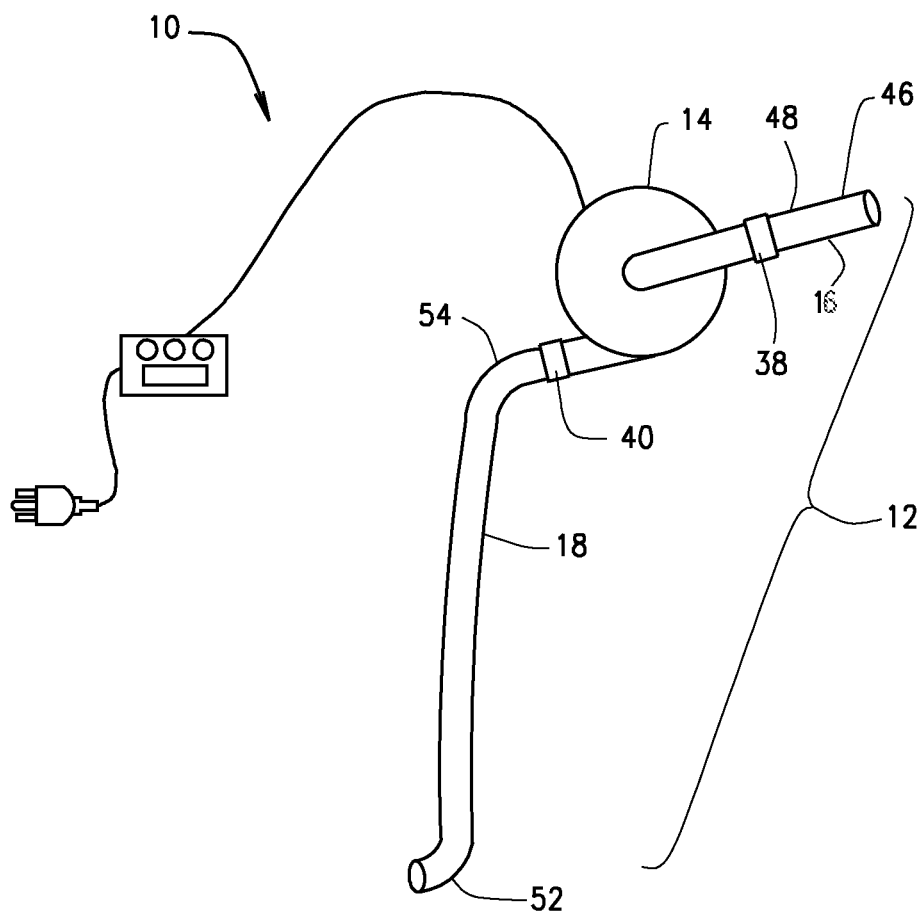
FIG. 1A is a schematic view of a pump-conduit assembly of a system and method in accordance with a first embodiment of the present invention.

The systems and components of the present application relate to a method for persistently increasing the overall diameter and the lumen diameter of veins and arteries. More specifically, in various embodiments, the present application relates to a method for pumping blood in a way (such as introducing blood or withdrawing blood from a selected peripheral vein or peripheral artery), such that the diameter of selected veins or arteries is persistently increased. The methods disclosed herein, may also increase the mean blood speed and/or the peak blood speed, as well as the mean wall shear stress and/or the peak wall shear stress in selected segments of veins or arteries for a period of time sufficient to persistently increase the overall diameter and the lumen diameter of selected segments of the veins or arteries. The methods may therefore be useful to create vascular access sites for hemodialysis, bypass grafts, or perform other vascular surgeries or procedures wherein a larger vein or artery diameter and/or a larger vein or artery length is desirable.

In various embodiments, the methods and systems described herein are provided such that the velocity of the blood in a peripheral vein or artery and the wall shear stress (WSS) on the endothelium of the peripheral vein or artery is increased by using a pump. Methods and systems are also described that remove or "pull" blood from a donating vessel such that the velocity of the blood and the WSS increased in the donating vessel, either an artery or a vein.

Preferred embodiments of the present invention will now be explained with reference to the drawings. It will be apparent to those skilled in the art from this disclosure that the following description of the embodiments of the present invention is provided for illustration only and not for limiting the invention as defined by the appended claims and their equivalents.

Referring initially to FIGS. 1-4, a system 10 to increase the overall diameter of peripheral veins is illustrated as used for a patient 20. The system 10 draws deoxygenated venous blood from the patient's venous system 22 and discharges that blood into the accepting peripheral vein 30. The system 10 also increases the speed of blood in the accepting peripheral vein 30 and increases the WSS exerted on the endothelium of the accepting peripheral vein 30, to persistently increase the diameter of the accepting peripheral vein 30 located, for example, in an arm 24 or a leg 26. The diameter of blood vessels such as peripheral veins can be determined by measuring the diameter of the lumen, which is the open space at the center of blood vessel where blood is flowing or measuring the overall diameter of the vessel, which includes both the center of the blood vessel where blood is flowing and the wall of the blood vessel.

The term "persistent increase", "persistently increased", or "persistent dilation" when used to describe a change in the overall diameter or lumen diameter of an artery or vein, is used herein to mean that even if a blood pump is turned off an increase in overall diameter or lumen diameter of a vessel can still be observed, when compared to the overall diameter or lumen diameter of the vessel prior to the period of blood pumping. That is, the overall diameter or lumen diameter of the vessel has become larger independent of the pressure generated by the blood pump.

For the purpose of this application, the diameter of the blood vessel lumen through which blood flows is referred to as the "lumen diameter." The diameter of blood vessels can also be determined by measuring the diameter in a manner that includes the wall of the blood vessel. For the purpose of this application, this measurement is referred to as the "overall diameter." The invention relates to simultaneously and persistently increasing the overall diameter and lumen diameter of a peripheral vein or artery by moving blood (preferably with low pulsatility) into the peripheral accepting vein, thereby increasing the speed of the blood in the peripheral accepting vein and increasing the WSS on the endothelium of the peripheral accepting vein. Systems and methods are described wherein the speed of the blood in a peripheral accepting vein and the WSS on the endothelium of the peripheral accepting vein is increased by using a pump. Preferably, the pump actively discharges blood into the peripheral accepting vein, in a manner where the pumped blood has reduced pulsatility, such as when the pulse pressure is lower than the pulse pressure of blood in a peripheral artery. For example, the pump may remove or pull blood from a vessel or discharge or push blood to a vessel such that the increased WSS exerted on the vessel causes a persisted increase in the overall diameter and the lumen diameter. "Pulsatility" and "pulsatility index", as used herein refer to a measure of the variability of blood speed in a vessel, equal to the difference between the peak systolic and minimum diastolic velocities divided by the mean speed during the cardiac cycle.

The systems and methods described herein increase the mean and peak WSS levels in a peripheral vein. Normal WSS for veins ranges between 0.076 Pa and 0.76 Pa. The systems and methods described herein are configured to increase the mean WSS level in the accepting peripheral vein to range from about 0.76 Pa and 23 Pa, preferably to a range between 2.5 Pa and 10 Pa. In certain circumstances, a sustained mean WSS less than 0.76 Pa may increase the overall diameter and lumen diameter of veins but in an amount too small and at a rate too slow to be widely accepted in clinical practice. Sustained mean WSS levels and/or peak WSS levels greater than 23 Pa are likely to cause denudation (loss) of the endothelium of the vein, which is known to retard the persistent increase in the overall diameter and lumen diameter of blood vessels in response to increases in blood speed and WSS. The methods of the present application relate to pumping blood for any amount of time that is sufficient to cause dilation. For example, pumping blood in a manner that increases WSS to the desired range for about 1 and 84 days or preferably between about 7 and 42 days, produces an amount of persistent increase in the overall diameter and lumen diameter in the accepting peripheral vein such that veins that were initially ineligible or suboptimal for use as a hemodialysis access site or bypass graft due to small vein diameter become usable or more optimal. In one embodiment, the blood pumping process may be performed in a static manner for a period of time. For example, the process may be performed for a period of 42 days and then the accepting vein or artery is used to create a hemodialysis access site. In this example, a blood pump may be implanted at a suitable location and then activated to discharge blood into a vessel and/or remove blood from a vessel for a period of time without any subsequent adjustments.

In various other embodiments, the blood pumping process may be monitored and adjusted periodically, either manually or automatically. For example, pump parameters (such as pump speed or impeller revolutions per minute) may be adjusted every second, minute, hour, day, multiple days, week, or multiple weeks (or at another time interval) to account for changes such as increases in the overall diameter and lumen diameter of the target vessel prior to achieving the desired persistent increase in overall diameter and lumen diameter. The system may include a software program that analyzes information collected by the system and automatically adjusts pump parameters (such as pump speed, impeller revolutions per minute, or outflow conduit pressure) to account for changes (such as a persistent increased overall diameter and lumen diameter in the target vessel) prior to achieving the desired persistent increased overall diameter and lumen diameter in the target vessel. For the purpose of this application, "target vessel", "target blood vessel", "target vein", or "target artery" means a specific segment of artery or vein that is intended to experience a persistently increased overall diameter and lumen diameter when a pump-conduit assembly is implanted, configured, and operated in such a way as to result in that persistent increase in overall diameter and lumen diameter of the specific segment of artery or vein.

The systems and methods described herein also increase the mean speed and the peak speed of blood in peripheral veins and peripheral arteries. At rest, the mean speed of blood in the cephalic vein in humans is generally in a range between 5 and 9 cm/s (0.05 and 0.09 m/s). For the systems and methods described herein, the mean speed of blood in the peripheral vein is increased to a range between 10 cm/s and 120 cm/s (0.1 and 1.2 m/s), preferably to a range between 25 cm/s and 100 cm/s (0.25 m/s and 1.0 m/s), depending on the desired rate of increase in overall diameter and lumen diameter of the treated vein. Depending on the initial diameter of peripheral vein and the desired post-treatment diameter of the peripheral vein, the mean blood speed is increased for between 1 day and 84 days, or preferably between 7 days and 42 days, to induce a persistent increase in the overall diameter and lumen diameter of the peripheral vein such that veins that were initially ineligible or suboptimal for use as a hemodialysis access site or bypass graft due to a small vein diameter become usable or more optimal. This can also be accomplished by intermittently increasing mean blood speed during the treatment period, with intervening periods of normal mean blood speed.

At rest, the mean speed of blood in the brachial artery is generally in a range between 10 and 15 cm/s (0.1 and 0.15 m/s). For the systems and methods described herein, the mean speed of blood in the peripheral artery is increased to a range between 10 cm/s and 120 cm/s (0.1 and 1.2 m/s), preferably to a range between 25 cm/s and 100 cm/s (0.25 and 1.0 m/s), depending on the desired rate of increase in overall diameter and lumen diameter of the treated artery. Depending on the initial diameter of artery and the desired post-treatment diameter of the artery, the mean blood speed is increased for between 1 day and 84 days, or preferably between 7 days and 42 days to induce a persistent increase in the overall diameter and lumen diameter of the peripheral donating artery such that arteries that were initially ineligible or suboptimal for use as a hemodialysis access site or bypass graft due to a small artery diameter become usable or more optimal. This can also be accomplished by intermittently increasing mean blood speed during the treatment period, with intervening periods of normal mean blood speed.

Studies have shown baseline hemodynamic forces and changes in hemodynamic forces within veins and arteries play a vital role in determining the overall diameter and lumen diameter of those veins and arteries. For example, persistent increases in blood speed and wall shear stress (WSS) can lead to a persistent increase in the overall diameter and lumen diameter of veins and arteries. The elevated blood speed and WSS are sensed by endothelial cells, which trigger signaling mechanisms that result in stimulation of vascular smooth muscle cells, attraction of monocytes and macrophages, and synthesis and release of proteases capable of degrading components of the extracellular matrix such as collagen and elastin. As such, the present invention relates to increasing blood speed and WSS for a period of time sufficient to result in vein and artery remodeling and a persistent increase in the overall diameter and lumen diameter of treated veins and arteries.

Assuming Hagen-Poiseuille blood flow in the vessel (i.e. a laminar flow with a fully developed parabolic velocity profile), then WSS can be determined using the equation:

$$WSS(Pa) = 4Q\mu/\pi R^3, \text{ where:}$$

Q=flow rate (m$^3$/s)
μ=viscosity of blood (Pa/s)
R=radius of vessel (m)

The systems and methods described herein increase the WSS level in peripheral veins and arteries. Normal mean WSS for veins ranges between 0.076 Pa and 0.76 Pa. For a persistent increase in the overall diameter and lumen diameter of veins, the systems and methods described herein increase the mean WSS level to a range between 0.76 Pa and 23 Pa, preferably to a range between 2.5 Pa and 7.5 Pa. Normal mean WSS for arteries ranges between 0.3 Pa and 1.5 Pa. For persistent increases in the overall diameter and lumen diameter of arteries, the systems and methods described herein increase the mean WS S level to a range between 1.5 Pa and 23 Pa, preferably to a range between 2.5 Pa and 10 Pa. Preferably, the mean WSS is increased for between 1 day and 84 days to induce a persistent increase in the overall diameter and lumen diameter in the target vessel such that vessels that were initially ineligible or suboptimal for use as a hemodialysis access site or bypass graft due to a small vein or artery diameter become usable or more optimal. This can also be accomplished by intermittently increasing mean WSS during the treatment period, with intervening periods of normal mean WSS.

In certain circumstances, mean WSS levels lower than 0.76 Pa in the accepting or donating peripheral vein may increase the overall diameter and lumen diameter of these vessels, but to an extent too small and at a rate too slow to be acceptable for routine clinical practice. Similarly, mean WSS levels lower than 0.3 Pa in the donating peripheral artery may increase the overall diameter and lumen diameter of these vessels, but to an extent too small and at a rate too slow to be acceptable for routine clinical practice. WSS levels in accepting or donating peripheral veins or in the donating arteries higher than about 23 Pa are likely to cause denudation (loss) of the endothelium of the veins and arteries. Denudation of the endothelium of blood vessels is known to retard persistent increases in the overall diameter and lumen diameter of blood vessels despite increases in blood speed and WSS. The increased WSS induces a sufficient persistent increase in the overall diameter and lumen diameter in the treated veins and arteries, such that those that were initially ineligible or suboptimal for use as a hemodialysis access site or bypass graft due to a small vessel diameter become usable or more optimal. The diameter of the accepting vein can be determined intermittently, such as every 1-14 days for example, to allow for pump speed adjustment in order to optimize the persistent increase in the overall diameter and lumen diameter of the vein during the treatment period.

The systems and methods described herein also increase the speed of blood in peripheral veins and in certain instances, peripheral arteries. At rest, the mean speed of blood in the cephalic vein in humans is generally between 5 and 9 cm/s (0.05 and 0.09 m/s). For the systems and methods described herein, the mean speed of blood in the peripheral vein is increased to a range between 10 cm/s and 120 cm/s (0.1 and 1.2 m/s), preferably to a range between 25 cm/s and 100 cm/s (0.25 and 1.0 m/s), depending on the initial diameter of vein, the desired post-treatment diameter of the vein, and the length of time of treatment (with elevated mean WSS) is planned.

At rest, the mean speed of blood in the brachial artery is generally between 10 and 15 cm/s (0.1 and 0.15 m/s). For the systems and methods described herein, the mean speed of blood in the peripheral artery is increased to a range between 10 cm/s and 120 cm/s (0.1 and 1.2 m/s), preferably to a range between 25 cm/s and 100 cm/s (0.25 and 1.0 m/s), depending on the initial diameter of artery, the desired post-treatment diameter of the artery, and the length of time of treatment (with elevated WSS) is planned. Preferably, the blood speed is increased for between 1 day and 84 days, or preferably, between 7 and 42 days, to induce a persistent increase in the overall diameter and lumen diameter in the peripheral accepting or donating vein or artery such that veins and arteries that were initially ineligible or suboptimal for use as a hemodialysis access site or bypass graft due to a small vein diameter become usable or more optimal. Mean blood speed levels in the accepting or donating peripheral vein or in the donating artery lower than 15 cm/s (0.15 m/s) may, under some circumstances, increase overall the overall diameter and lumen diameter of these vessels, but to an extent too small and at a rate too slow to be acceptable for routine clinical practice. Blood speed levels in accepting or donating peripheral veins or in donating arteries higher than about 100 cm/s (1 m/s) are likely to cause denudation (loss) of the endothelium of the veins and arteries. Denudation of the endothelium of blood vessels is known to retard a persistent increase in the overall diameter and lumen diameter despite increases in blood speed. The increased blood speed induces a sufficient persistent increase in the overall diameter and lumen diameter in the veins and arteries, such that those that were initially ineligible or suboptimal for use as a hemodialysis access site or bypass graft due to a small diameter become usable or more optimal.

The blood pumping process may be monitored and adjusted periodically. For example, pump parameters (such as pump speed, impeller revolutions per minute, or conduit outflow pressure) may be adjusted every seven days (or at other intervals) to account for changes (such as an increased overall diameter and lumen diameter) in the target peripheral vein or artery prior to achieving the desired persistent increase in the overall diameter and lumen diameter. As an additional example, the system may include a software program that analyzes information collected by the system and automatically adjusts pump parameters (such as pump speed, impeller revolutions per minute, or outflow conduit pressure) to account for changes (such as an increased overall diameter and lumen diameter) in the peripheral vein or artery prior to achieving the desired persistent increase in the overall diameter and lumen diameter.

Figure 2A:
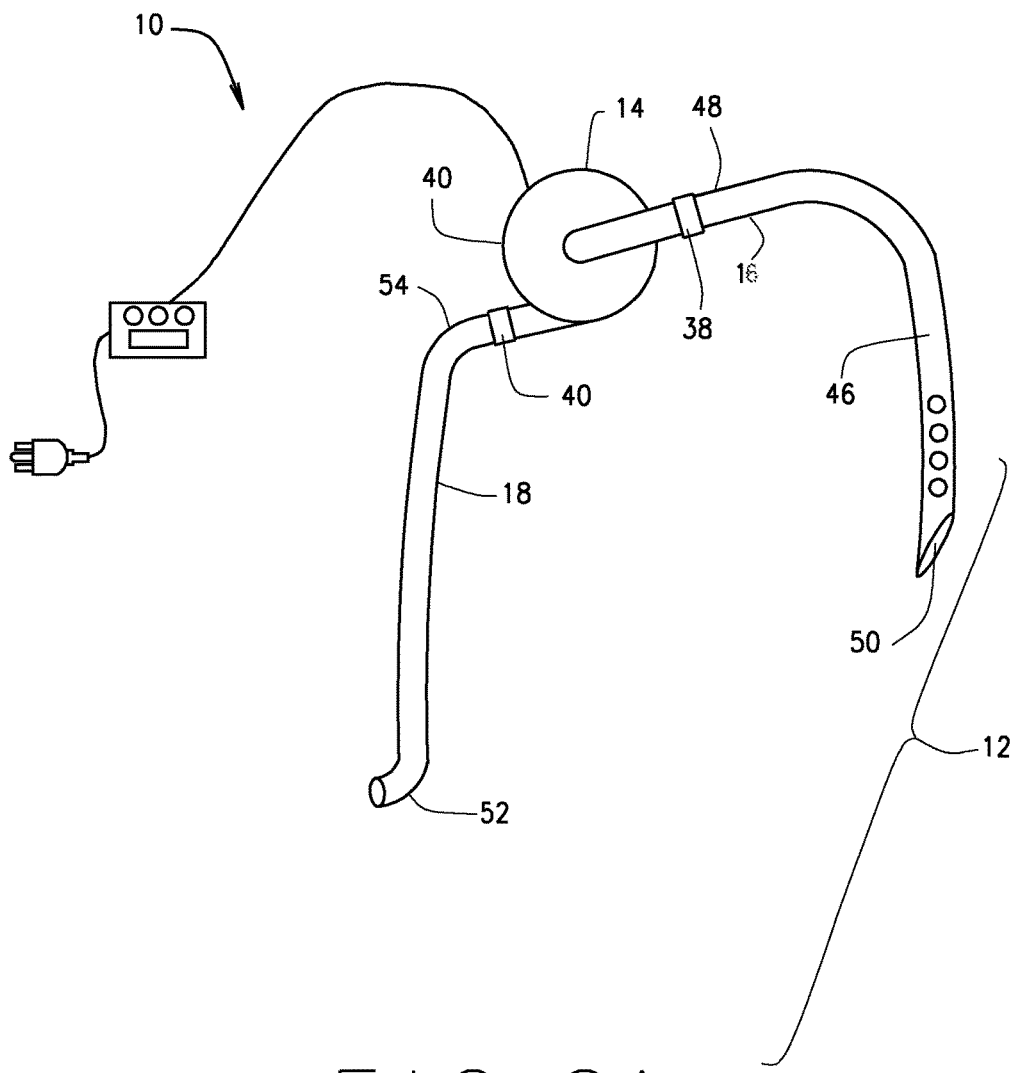
FIG. 2A is a schematic view of a pump-conduit assembly of a system and method in accordance with a second embodiment of the present invention.
Figure 2B:
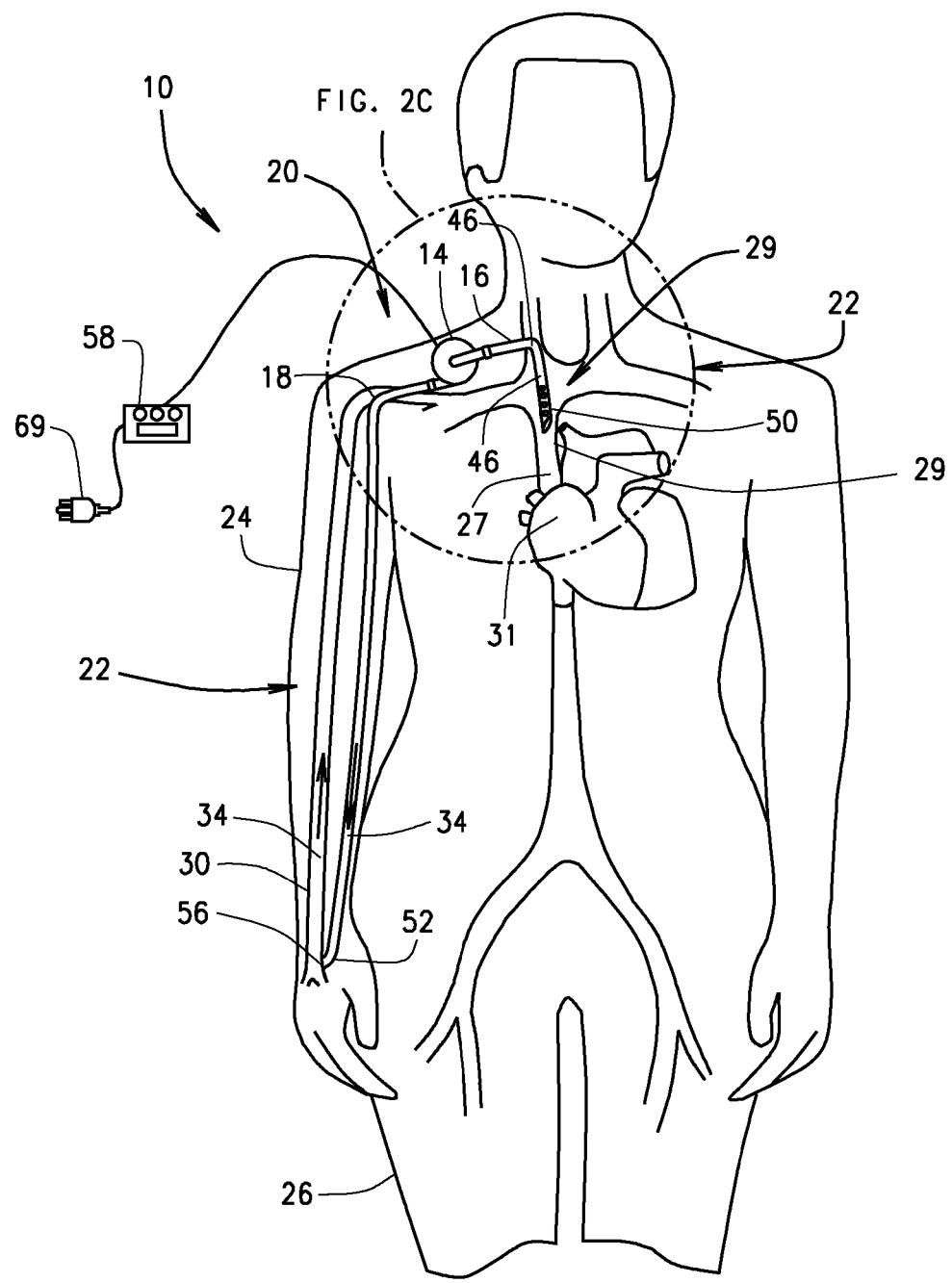
FIG. 2B is a schematic view of the pump-conduit assembly of FIG. 2A as applied to a circulatory system of a patient in accordance with the second embodiment of the present invention.
Figure 2C:
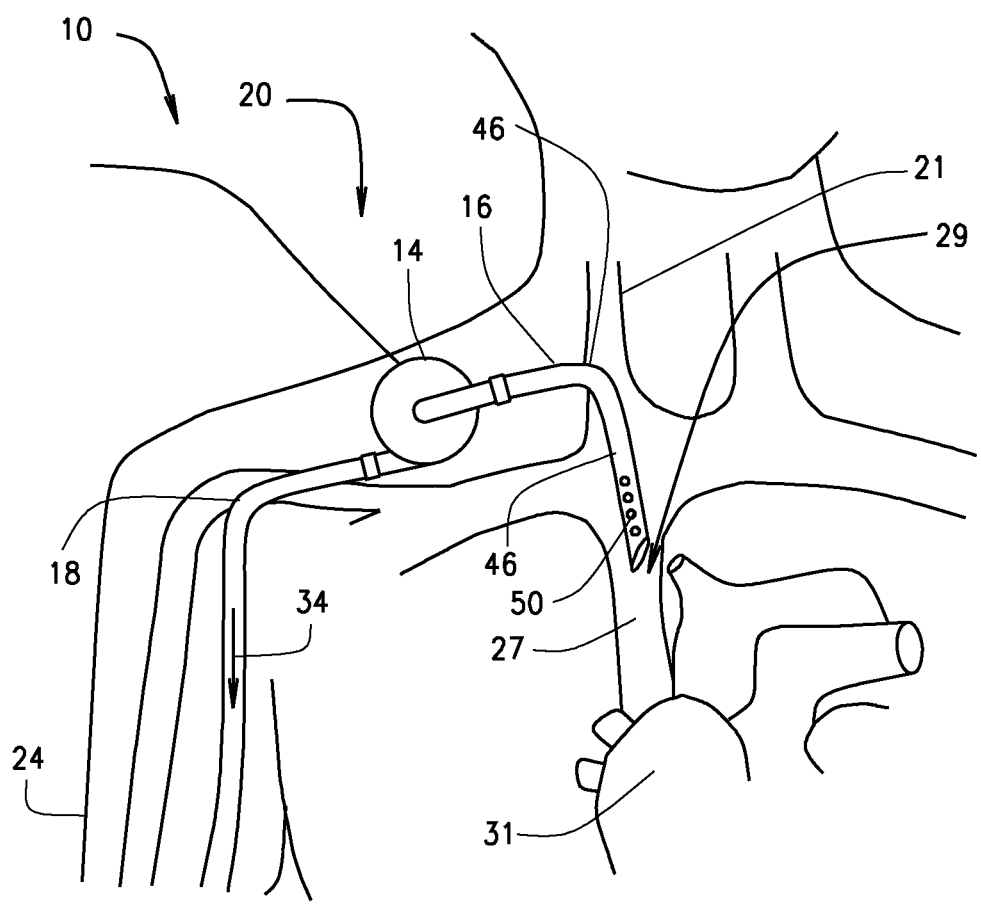
FIG. 2C is a magnified view of a portion of FIG. 2B.
Figure 3:
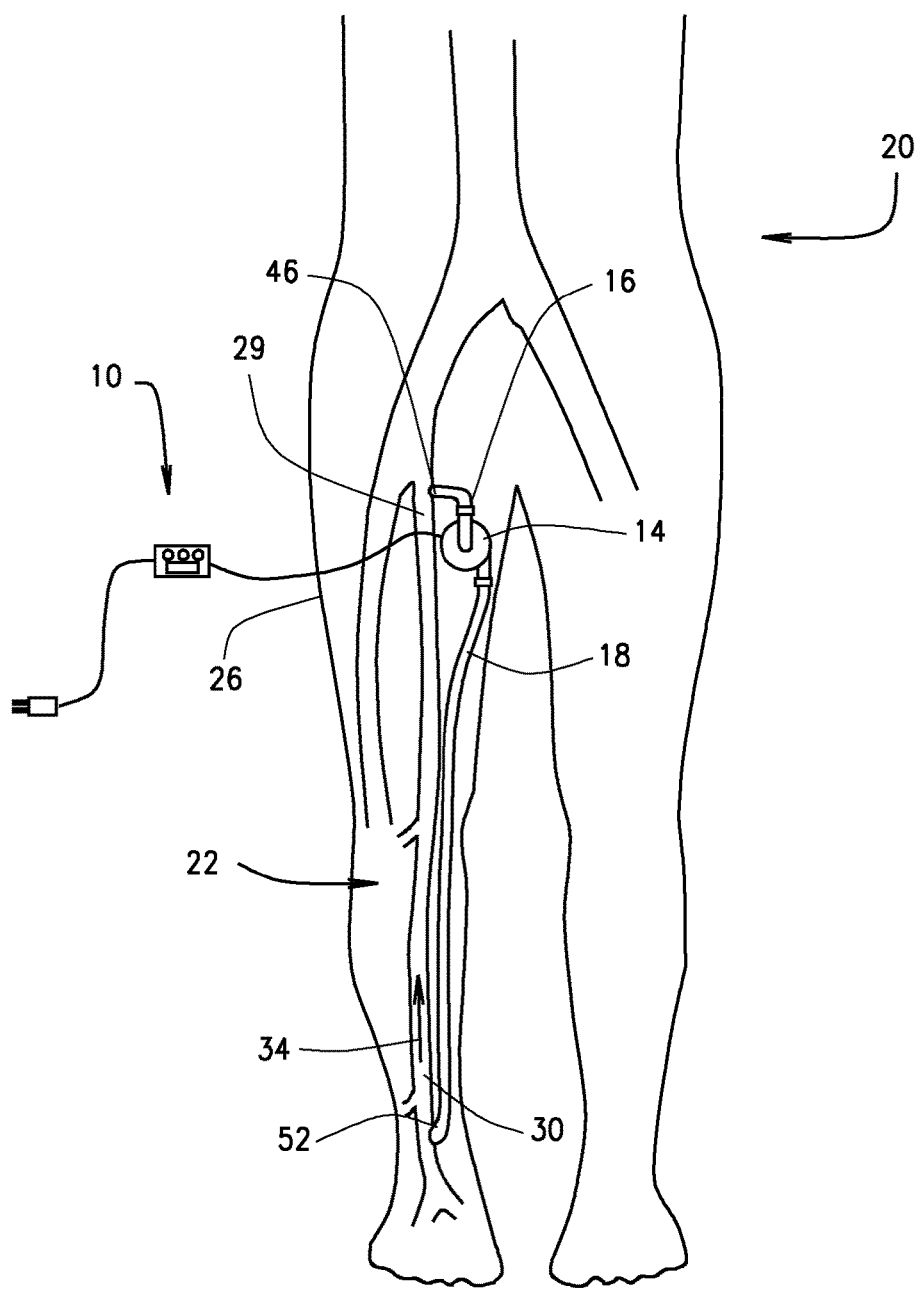
FIG. 3 is a schematic view of a pump-conduit assembly of a system and method as applied to a circulatory system of a patient in accordance with a third embodiment of the present invention.

Referring to FIGS. 1-3, the system 10 includes a pump-conduit assembly 12 for moving deoxygenated venous blood from a donating vein 29 of the venous system 22 of the patient 20 to the peripheral or accepting vein 30. In various embodiments, the peripheral or accepting vein 30 may be a cephalic vein, radial vein, median vein, ulnar vein, antecubital vein, median cephalic vein, median basilic vein, basilic vein, brachial vein, lesser saphenous vein, greater saphenous vein, or femoral vein. Other veins that might be useful in the creation of a hemodialysis access site or bypass graft, or other veins useful for other vascular surgery procedures requiring the use of veins may be used. The pump-conduit assembly 12 delivers the deoxygenated blood to the peripheral or accepting vein 30, also known as the target vein. The increased speed of the blood 34 and the increased WSS in the peripheral vein 30 causes the peripheral accepting vein 30 to enlarge over time, which may be manifest as increased overall diameter, increased lumen diameter, or increased length. Thus, the system 10 and method 100 (referring to FIGS. 10-11) of the present invention advantageously persistently increase the diameter of the peripheral accepting vein 30 so that it can be used, for example, to construct an AVF or AVG access site for hemodialysis or as a bypass graft.

As used herein, deoxygenated blood is blood that has passed through the capillary system and had oxygen removed by the surrounding tissues and then passed into the venous system 22. A peripheral vein 30, as used herein, means any vein with a portion residing outside of the chest, abdomen, or pelvis. In the embodiment shown in FIGS. 1B and 2B, the peripheral accepting vein 30 is the cephalic vein. However, in other embodiments, the peripheral accepting vein 30 may be a radial vein, median vein, ulnar vein, antecubital vein, median cephalic vein, median basilic vein, basilic vein, brachial vein, lesser saphenous vein, greater saphenous vein, or femoral vein. In addition to a peripheral vein, other veins that might be useful in the creation of a hemodialysis access site or bypass graft or other veins useful for other vascular surgery procedures requiring the use of veins may also be used, including those residing within the chest, abdomen, and pelvis.

In order to reduce the pulsatility of blood that is directed into a peripheral accepting vein and/or provide low-pulsatile blood flow to a peripheral accepting vein, a number of pulsatility dampening techniques may be used. Pulsatility is dampened in order to reduce cyclic stretch of smooth muscle cells in the accepting vein, which has been shown to cause increased venous smooth muscle proliferation, a key component of venous neointimal hyperplasia and vein stenosis. By way of example, and not limitation, such techniques include tuning the head-flow characteristics of a blood pump, adding an elastic reservoir or Windkessel segment to the inflow or outflow conduits, adding compliance to the inflow or outflow conduits, modulating the pump speed, such as a modulation that increases pump speed during diastole and decreases pump speed during systole, or adding counterpulsation to the inflow or outflow conduits or the pump.

An AVF created using the cephalic vein at the wrist is a preferred form of vascular access for hemodialysis, but this vein is frequently of inadequate or suboptimal diameter to facilitate the creation of an AVF in this location. Thus, the present invention is advantageous to creating AVFs in the wrist of ESRD patients and increasing the percentage of ESRD patients that receive hemodialysis using a wrist AVF as a vascular access site.

The pump-conduit assembly 12 includes a blood pump 14 and synthetic conduits 16 and 18, i.e. an inflow conduit 16 and an outflow conduit 18. Blood pumps have been developed as a component of ventricular assist devices (VADs) and have been miniaturized to treat adult patients with moderate heart failure and pediatric patients.

In one embodiment, a blood pump system having a pump suitable for increasing blood speed and WSS in peripheral arteries and veins, a conduit system, a control system, and a power source, as described in related co-filed U.S. patent application entitled "Blood Pump Systems and Methods," may be used. In this embodiment, the pump is a centrifugal pump and pump system that may fluidly connect to one blood vessel or location in the cardiovascular system (including but not limited to central and peripheral arteries and veins, and the right atrium) and remove blood from a first blood vessel or location in the cardiovascular system and fluidly connect to a second blood vessel or location in the cardiovascular system (including but not limited to central and peripheral arteries and veins, and the right atrium) and move blood into that second blood vessel or location in the cardiovascular system. The conduit system includes an inflow conduit to carry blood from a blood vessel or location in the cardiovascular system to the pump and an outflow conduit to carry blood from the pump to a second blood vessel or location in the cardiovascular system. The blood pump system also includes a control system for modulating the parameters of the pump and the system, including but not limited to, the speed of the blood pump, the speed of the impeller, and the outflow conduit pressure. For certain embodiments, the control system includes sensors in the blood pump, conduits, or in the vascular system of the patient that measure at least one of: the power or current necessary to operate the pump under certain operating conditions, a blood speed, a rate of blood flow, a resistance to blood flow into or out of a peripheral blood vessel, a blood pressure or pulse pressure (in the inflow conduit, outflow conduit, or in an adjacent blood vessel), a pulsatility index, and combinations thereof. The blood pump system is primarily configured to pump a sufficient amount of blood for a sufficient period of time such that a desired and elevated WSS and blood speed is achieved within a target blood vessel and maintained for a period of time sufficient to result in an increase in the overall diameter, lumen diameter, or length of the target blood vessel. The WSS can be determined using the average flow rate through the pump system and the diameter of the target blood vessel. In this setting, the average flow rate out of the pump can be estimated from a measurement of the power necessary to drive the pump. In this setting, the assumption is made that all of the flow is coming from (for a donating vessel) or going to (for a peripheral accepting vein) the target vein.

Figure 9:
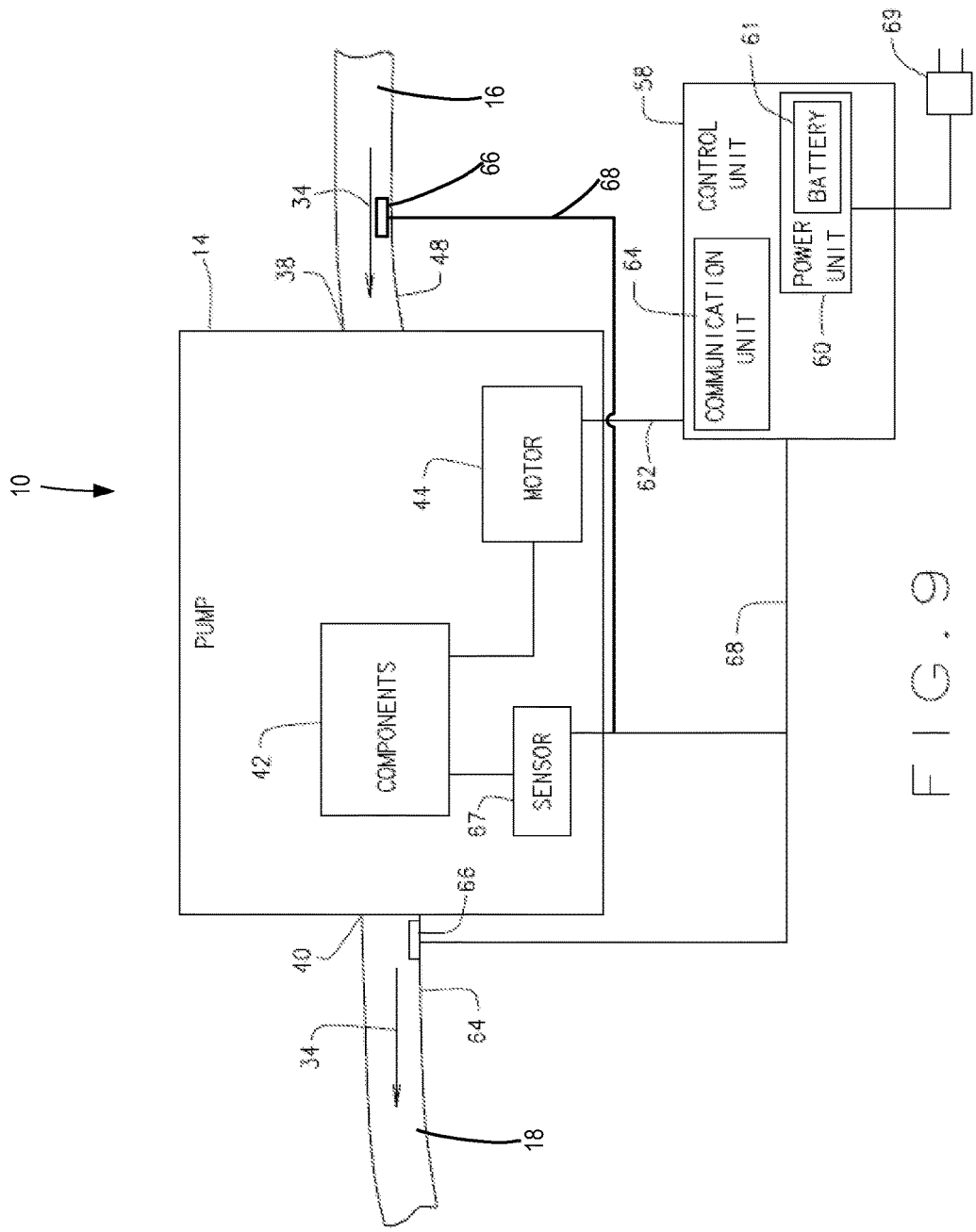
FIG. 9 is a schematic diagram of a pump operated in conjunction with a control unit for use in any of the above-mentioned embodiments.

The pump can be implanted or remain external to the patient and is usually connected to one or more conduits, a controller, and a power source. Referring to FIG. 9, a schematic diagram of the pump system 10 is illustrated. The pump 14 can be a rotary pump such as an axial, mixed flow, or centrifugal pump. Without recognizing specific limitations, the bearing for the pump 14 can be constructed with magnetic fields, with hydrodynamic forces, or using a mechanical contact bearing such as a double-pin bearing. Pumps used in pediatric VAD systems or other low flow VAD systems can be used, including the blood pump system described above. Alternatively, the pump 14 can be an extracardiac pump such as that shown and described in U.S. Pat. Nos. 6,015,272 and 6,244,835, both of which are hereby incorporated herein by reference. These pumps are suitable for use in the system 10 and for carrying out the methods 100, as shown in FIGS. 10-14, of the present invention. The pump 14 has an inlet 38 to receive deoxygenated blood drawn into the inflow conduit 16 and an outlet 40 for blood flow 34 to exit the pump 14 and move into the outflow conduit 18. In regards to pumps used in pediatric VAD systems or other low flow VAD systems suitable for use as pump 14 of the present invention, these pumps can be sized as small as about the size of a AA battery or the diameter of a United States half dollar or quarter, and can weigh as little as about 35 grams or less. These pumps are designed to pump about 0.05 to 1.0 L/min, 0.1 to 1.5 L/min, or 1.0 to 2.5 L/min, for example. For the pumps mentioned above which are designed to operate in the higher flow rate ranges, modifications to these pumps could be made to reduce this range to as low as 0.05 L/min for use in small diameter peripheral veins and arteries. The blood-contacting surfaces of the pump 14 could comprise $Ti_6Al_4V$, $Ti_6Al_7Nb$, or other commercially pure titanium alloys or metals, alternative titanium alloys, biocompatible ceramics such as alumina, silicon carbide or zirconia, or biocompatible polymers. In certain embodiments, the blood-contacting surface may have one or more coatings and surface treatments, including anti-thrombotic coatings that reduce the accumulation of thrombus on the blood-contacting surfaces. As such, any of a variety of pumping devices can be used so long as they can be fluidly connected to the vascular system and can safely pump a sufficient amount of blood such that the desired blood speed and WSS is achieved in the target blood vessel, such as an accepting vein or in a donating vein or donating artery, among others.

The pump 14 includes various components 42 and a motor 44, as shown in FIG. 9. The various components 42 and motor 44 can be those common to a VAD or to the pump of the blood pump system. For example, the components 42 include one or more of a shaft, impeller, impeller blades, bearings, stator vanes, rotor, or stator. The rotor can be magnetically levitated, or the rotor position can be controlled by hydrodynamic forces, or using a mechanical contact bearing such as a double-pin bearing. The motor 44 can include a stator, rotor, coil, and magnets. The motor 44 may be any suitable electric motor, such as a multi-phase motor controlled via pulse-width modulated current. In operation, the pump 14 may create a suction within the inflow catheter 16 to pull blood from a blood vessel, such as a peripheral artery peripheral vein 30, a central vein, or the right atrium 31.

The system 10 and methods 100 can use one or more of the pumps described in the following publications: The PediaFlow™ Pediatric Ventricular Assist Device, P. Wearden, et al., Pediatric Cardiac Surgery Annual, pp. 92-98, 2006; J. Wu et al., Designing with Heart, ANSYS Advantage, Vol. 1, Iss. 2, pp. s12-s13, 2007; and J. Baldwin, et al., The National Heart, Lung, and Blood Institute Pediatric Circulatory Support Program, Circulation, Vol. 113, pp. 147-155, 2006. Other examples of pumps that can be used as the pump 14 include: the Novacor, PediaFlow, Levacor, or MiVAD from World Heart, Inc.; the Debakey Heart Assist 1-5 from Micromed, Inc.; the HeartMate XVE, HeartMate II, HeartMate III, IVAD, PVAD, CentriMag, PediMag, or UltraMag from Thoratec, Inc.; the Impella, BVS5000, AB5000, or Symphony from Abiomed, Inc.; the Tandem-Heart from CardiacAssist, Inc.; the VentrAssist from Ventracor, Inc.; the Incor or Excor from Berlin Heart, GmbH; the Duraheart from Terumo, Inc.; the HVAD or MVAD from HeartWare, Inc.; the Jarvik 2000 Flowmaker or Pediatric Jarvik 2000 Flowmaker from Jarvik Heart, Inc.; the Gyro C1E3 from Kyocera, Inc.; the CorAide or PediPump from the Cleveland Clinic Foundation; the MEDOS HIA VAD from MEDOS Medizintechnik AG; the pCAS from Ension, Inc; the Synergy from Circulite, Inc; and, the BP-50 and BP-80 from Medtronic, Inc. The pumps can be monitored and adjusted manually or with a software program, application, or other automated system. The software program can automatically adjust the pump speed (including the revolutions per minute of the impeller) to maintain the desired blood speed and WSS in a target vessel such as an accepting vein, a donating artery, or a donating vein. Alternatively, the diameter of the target blood vessel and the blood flow in the blood pump system or the target blood vessel may be periodically checked and the pump may be manually adjusted to maintain the desired blood speed and WSS levels in the target blood vessel.

In one embodiment, the mean blood speed is determined by calculating an average of multiple discrete measurements of blood speed by summing the discrete measurements and dividing the total by the number of measurements. Mean blood speed can be calculated by taking measurements over a period of seconds, minutes, or hours.

In another embodiment, the mean wall shear stress (WSS) is determined by making a series of discrete measurements, making multiple discrete determinations of WSS (using those measurements), summing the discrete WSS determinations, and dividing the total by the number of determinations. Mean WSS can be calculated by taking measurements and making discrete WSS determinations over a period of seconds, minutes, or hours.

Blood received and pumped by the pump 14 travels through one or more of synthetic conduits 16 and 18. The synthetic conduits 16 and 18 are connected to the pump 14 using connectors that provide a secure leak-proof fluid connection to the pump. In one embodiment, the connectors are radially compressive connectors that compress the synthetic conduits 16 and 18 against barb-fittings incorporated into the inlet 38 and/or outlet 40 of the pump 14.

The synthetic conduits 16 and 18 can be of any material or combination of materials so long as the conduits 16 and 18 exhibit desired characteristics, such as flexibility, sterility, resistance to kinking, resistance to compression, and can be fluidly connected to a blood vessel via a surgical anastomosis or inserted into the lumen of a blood vessel, as needed. All or a portion of the synthetic conduits 16 and 18 may be comprised of materials commonly used to make hemodialysis catheters such as polyvinyl chloride, polyethylene, polyurethane, and/or silicone. All or portions of the synthetic conduits 16 and 18, as well as other portions of the system 10, may be reinforced with nitinol or another shape memory alloy or radially expansive metal or material. Preferably, a layer of braided nitinol is wrapped around the synthetic conduits 16 and 18 or incorporated into the walls of conduits. Alternately, a coil of nitinol may be wrapped around all or portions of the synthetic conduits 16 and 18 or incorporated therein. All or a portion of the synthetic conduits 16 and 18 may be comprised of polytetrafluoroethylene (PTFE), expanded polytetrafluoroethylene (ePTFE), and/or Dacron, preferentially reinforced so that these segments of the synthetic conduits 16 and 18 are less susceptible to kinking and obstruction. In addition, the synthetic conduits 16 and 18 preferably exhibit characteristics needed for tunneling (as desired) such as comprising lubricious external surface coatings such as Harmony™ advanced lubricity coatings, and have luminal surfaces that are resistant to thrombosis. The luminal surfaces may be coated with an antithrombotic agent or material. For example, the luminal surfaces may be coated with Astute®, a heparin based antithrombotic coating by BioInteractions Ltd., or Applause™ heparin coating by SurModics, Inc.

As another example, all or portions of the synthetic conduits 16 and 18 can have an exterior layer composed of a different material than the luminal layer. The synthetic conduits 16 and 18 can be coated with silicon to aid in removal from the body and avoid latex allergies. In addition, the external surfaces of the synthetic conduits 16 and 18 may have an antimicrobial coating. For example, the external surfaces of the synthetic conduits 16 and 18 or the external surfaces of the pump or lead may be coated with Avert®, a surface-active antimicrobial coating by BioInteractions Ltd.

In certain embodiments, the connection between the synthetic conduit 16 or 18 and the vein 29 or 30 is made using a conventional surgical anastomosis, using suture in a running or divided fashion, henceforth described as an "anastomotic connection." An anastomotic connection can also be made with surgical clips and other standard ways of making an anastomosis. In certain embodiments, a conduit is comprised of a segment made of materials commonly used to make hemodialysis catheters such as polyvinyl chloride, polyethylene, polyurethane, and/or silicone that is physically joined to a segment made of polytetrafluoroethylene (PTFE), expanded polytetrafluoroethylene (ePTFE), and/or Dacron that can be connected to a peripheral vein or artery by an anastomotic connection.

In other embodiments the portions of the inflow and outflow conduits 16 and 18 that are configured to be inserted into the lumen of the vascular system may have walls with are self-expanding or radially expansive (such as can be accomplished by incorporating nitinol) so that the diameter of the intravascular portion of the inflow and outflow conduits 16 and 18 will match the diameter of the vascular system at that location, such as is seen with the self-expanding segment of the GORE® Hybrid Vascular Graft.

Referring to FIG. 1, the inflow conduit 16 has a first end 46 configured to fluidly connect to a donating vein 29 or the right atrium 31 of the heart and a second end 48 configured to fluidly connect to the inlet 38 of the pump 14. The donating vein 29 can include an antecubital vein, basilic vein, brachial vein, axillary vein, subclavian vein, jugular vein, brachiocephalic vein, superior vena cava, lesser saphenous vein, greater saphenous vein, femoral vein, common iliac vein, external iliac vein, superior vena cava, inferior vena cava, or other veins capable of providing sufficient blood flow to the pump for the purpose of causing a persistent increase in the overall diameter and lumen diameter of the target vessel, in this case an accepting peripheral vein 30. The outflow conduit 18 has a first end 52 configured to fluidly connect to the peripheral accepting vein 30 and a second end 54 configured to fluidly connect to the outlet 40 of the pump 14. In various embodiments, the first end 46 of the inflow conduit 16 and the first end 52 of the outflow conduit 18 are chamfered at an angle between 15° and 75°, and preferably at 45°.

Figure 1B:
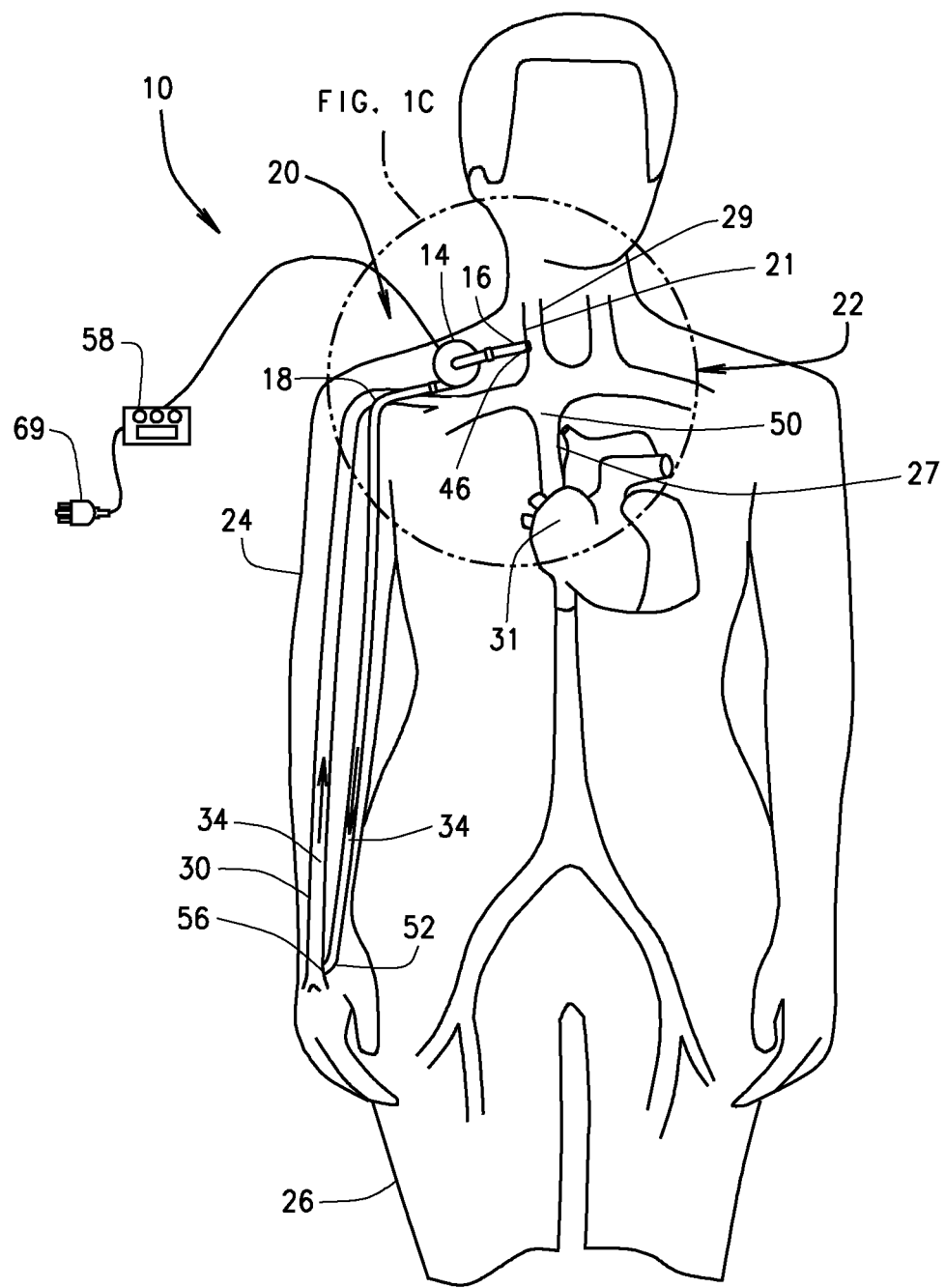
FIG. 1B is a schematic view of the pump-conduit assembly of FIG. 1A as applied to a circulatory system of a patient in accordance with the first embodiment of the present invention.
Figure 1C:
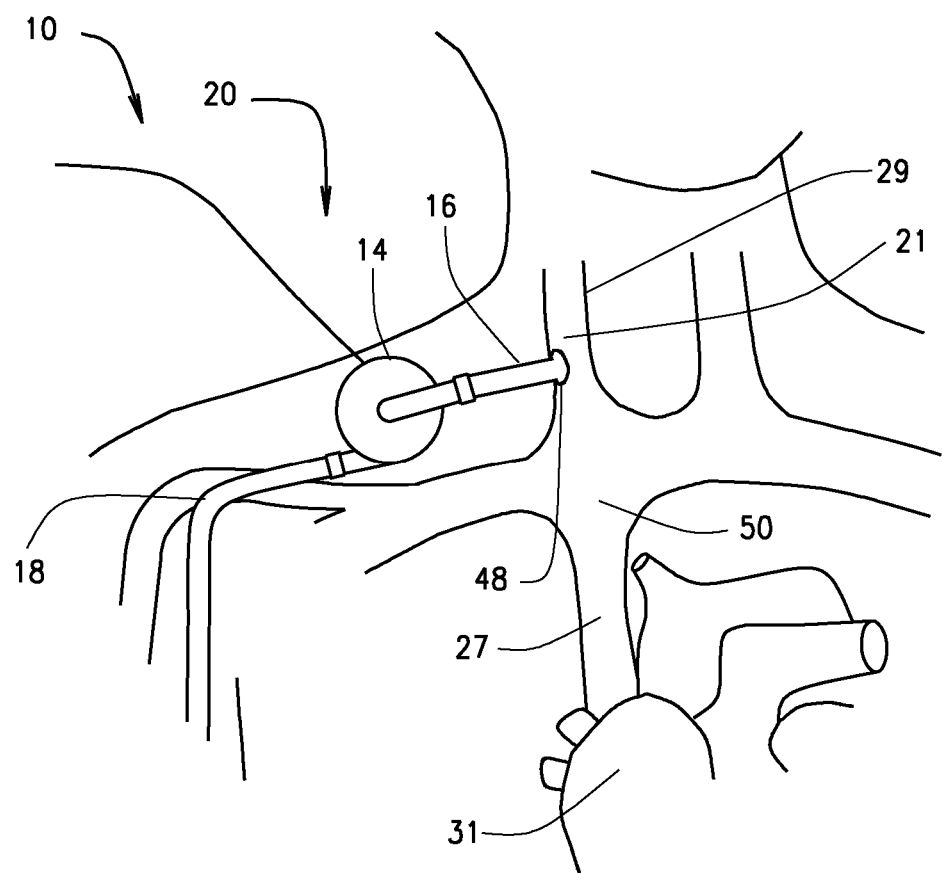
FIG. 1C is a magnified view of a portion of FIG. 1B.

The pump-conduit assembly 12 is configured to move blood from the donating vein 29 to the peripheral accepting vein 30 in a manner that increases the mean blood speed, the peak blood speed, and WSS in the target vein (in this case the peripheral accepting vein 30) to the desired level for a period of time sufficient to cause a persistent increase in the overall diameter and lumen diameter of the peripheral accepting vein. In certain embodiments, a portion of the synthetic conduits 16, 18 may be extracorporeal to the patient 20. Referring to FIGS. 1 and 3, the first end 46 of the inflow conduit 16 and the first end 52 of the outflow conduit 18 are configured for an anastomotic connection. As shown in FIGS. 1B and 1C, the first end 46 is fluidly connected to the internal jugular vein (which serves as the donating vein 29) via an anastomotic connection and the first end 52 of the outflow conduit 18 is fluidly connected to the cephalic vein (which serves as the peripheral accepting vein 30) via an anastomotic connection.

Referring to FIGS. 2A-2C, the first end 46 of the synthetic inflow conduit 16 is configured as a catheter. The fluid connection between the synthetic inflow conduit 16 and the venous system is made by positioning the tip of the catheter portion 50 of the synthetic inflow conduit into the superior vena cava 27, henceforth described as a "catheter connection." When a catheter connection is made with a donating vein 29 (in this case, the superior vena cava 27), the catheter portion 50 of the synthetic inflow conduit 46 may enter the venous system at any location where the vein lumen diameter is adequate to accept the catheter portion 50. The tip of the catheter portion 50 may be placed at any location where sufficient blood can be drawn into the catheter to provide the desired blood flow 34 to the accepting vein 30. Preferred locations for the tip of the catheter portion 50 include, but are not limited to a brachiocephalic vein, the superior vena cava 27, and the right atrium 31. In the embodiment illustrated in FIGS. 2B-2C, the system 10 draws deoxygenated blood from the superior vena cava 27 of the patient 20 and discharges it to the cephalic vein 30 in the arm 24.

In another embodiment shown in FIG. 3, the system 10 draws deoxygenated venous blood from donating vein 29 (in this case, the more proximal portion of the greater saphenous vein) and discharges it to the peripheral accepting vein 30 (in this case, a more distal portion of the greater saphenous vein) in the leg 26 thereby increasing the speed of blood and WSS in the accepting peripheral vein to the desired level and for a period of time sufficient to cause a persistent increase in the lumen diameter and overall diameter of the accepting greater saphenous vein 30. In settings where it may be desirable to increase retrograde venous flow into the blood pump system, one or more venous valves between connections of the inflow conduit, the donating vein, or the right atrium may be rendered incompetent to allow blood to flow in a retrograde direction in that segment of the donating vein and then flow into the inflow conduit. In the embodiment shown in FIG. 3, the inflow conduit 16 is fluidly connected to a proximal greater saphenous vein 29 of the patient 20 via an anastomotic connection. The pumping of blood into the peripheral accepting vein 30 (in this case the distal greater saphenous vein) and the increase in the mean blood speed, the peak blood speed, and the mean WSS continues for a period of time sufficient to cause a persistent increase in the overall diameter and lumen diameter of the accepting greater saphenous vein segment 30 to facilitate extraction and autotransplantation as part of a surgery to create a cardiac or peripheral bypass graft, or other surgery that requires autotransplantation of a portion of a patient's vein.

Figure 4A:
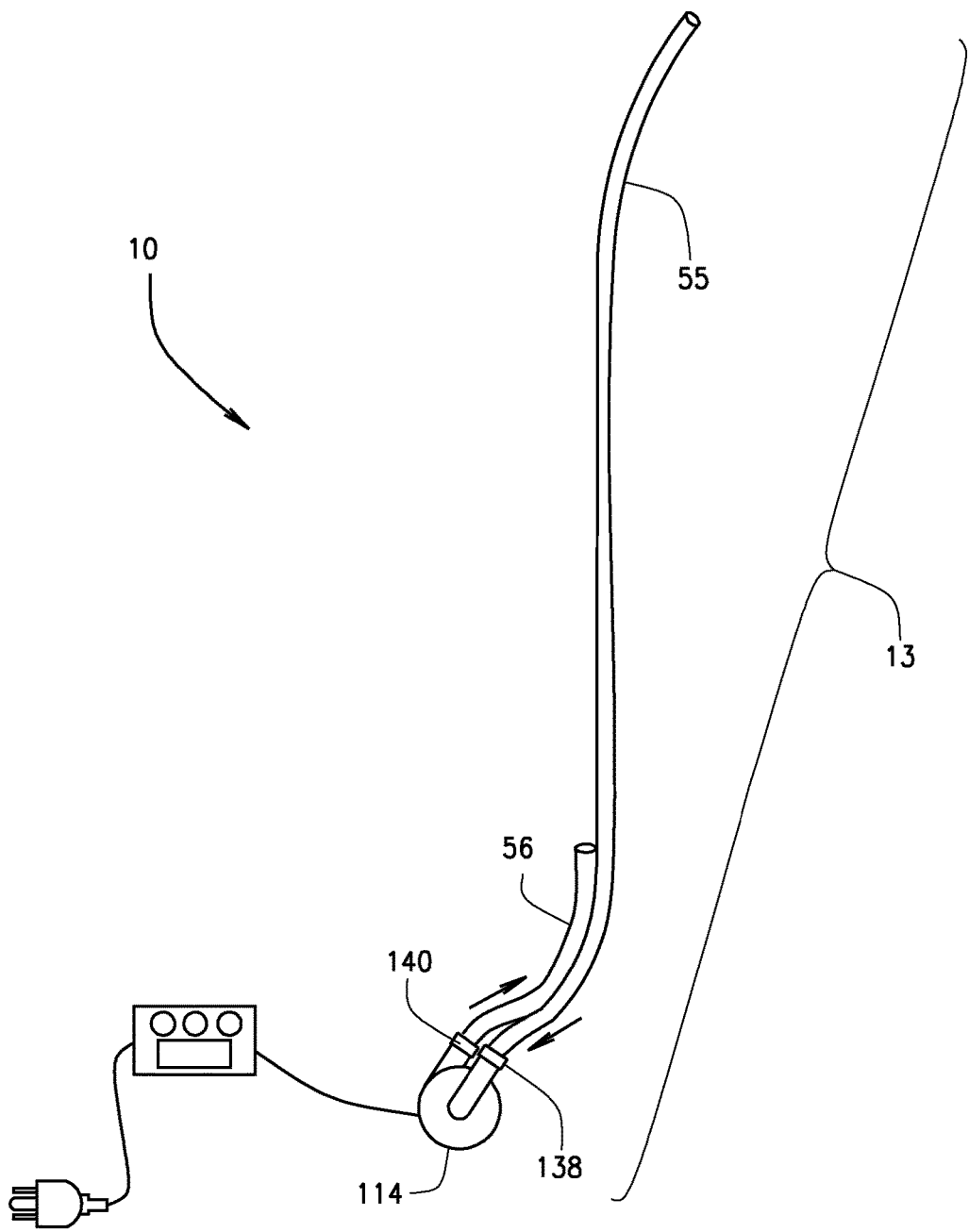
FIG. 4A is a schematic view of a pump-catheter assembly of a system and method in accordance with a fourth embodiment of the present invention.
Figure 4B:
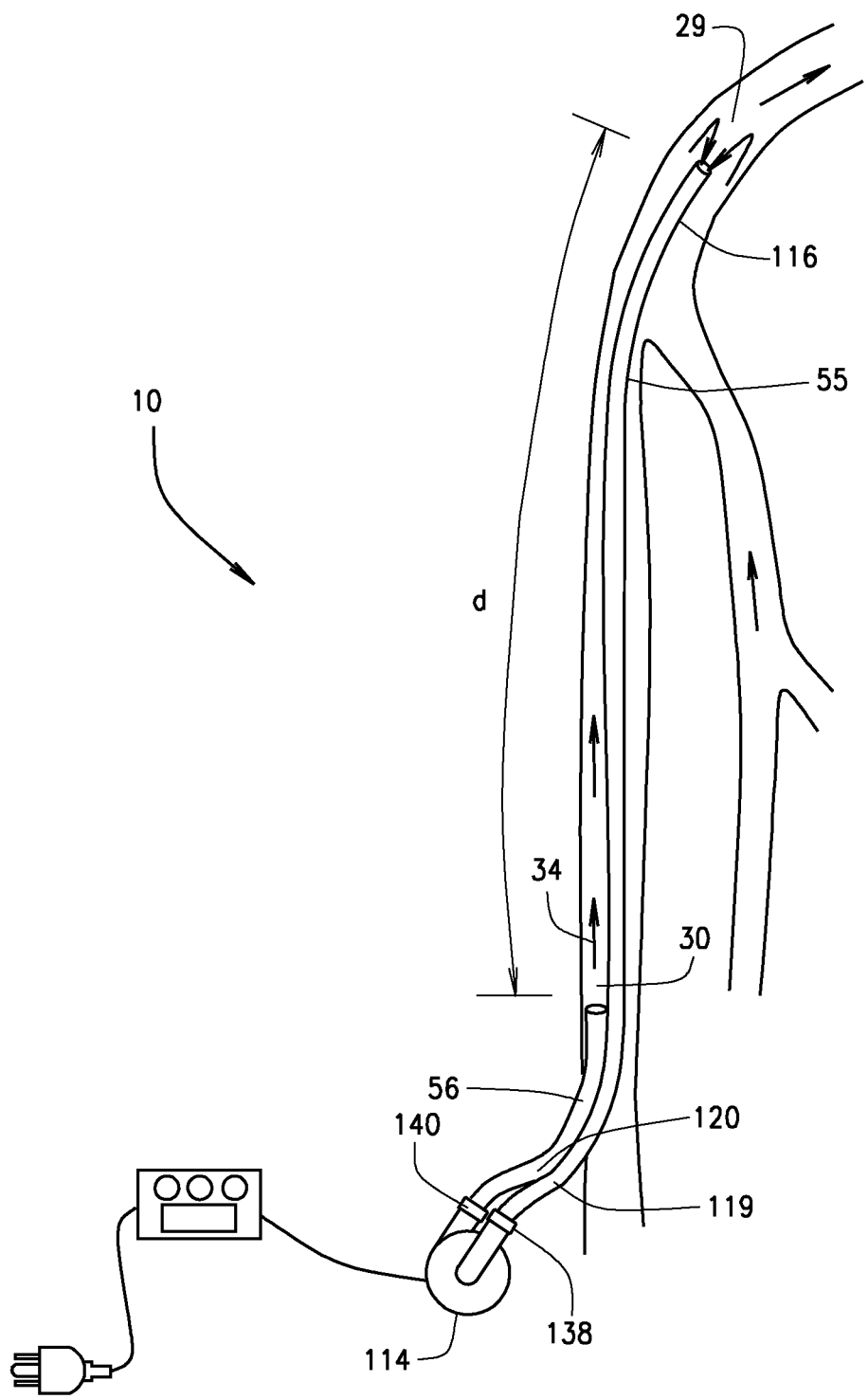
FIG. 4B is a schematic view of the pump-catheter assembly of FIG. 4A as applied to a circulatory system of a patient in accordance with the fourth embodiment of the present invention.

FIGS. 4A and 4B illustrate another embodiment of the system 10. Referring to FIG. 4A, in another embodiment, an extracorporeal or implanted pump 114 is attached to two specialized catheters which act as conduits, an inflow conduit 55, and an outflow conduit 56 to form a conduit-pump assembly (which can be alternatively described as a catheter-pump assembly) 13. The pump 114 draws deoxygenated blood into the lumen of the inflow conduit 55 from the donating vein 29 and then discharges the blood from the outflow conduit 56 and into the lumen of the peripheral accepting vein 30, thereby increasing the speed of blood and the WSS in the peripheral accepting vein 30.

Referring to FIGS. 4A and 4B, the pump-conduit (or pump-catheter) assembly 13 is configured to increase the blood speed and WSS in vein segment d. The inflow conduit 55 and the outflow conduit 56 may optionally be joined in all or some portions and can be percutaneously inserted into the lumen of the accepting peripheral vein 30, obviating the need for a more invasive surgical procedure. In certain embodiments, a portion of one or both conduits may be tunneled subcutaneously under the skin, with the tunneled segment being positioned between the intravascular segment and the extracorporeal segment, in order to reduce the risk of infection. Extracorporeal portions of the catheters 119 and 120 and the extracorporeal pump 114 can be affixed to the body. Alternatively, the pump and conduits can be implanted with the lead to the controller exiting the skin. The pump 114 may be connected to a power source and operated in a manner that increases blood speed 34 and WSS in segment d of the accepting peripheral vein 30 for a period of time sufficient to cause a persistent increase the overall diameter and lumen diameter of segment d. Once the desired amount of persistent increase in the overall diameter and lumen diameter has occurred in segment d of the accepting peripheral vein 30, the pump-conduit assembly 12 is removed and a surgical procedure can be performed to create a hemodialysis access site or bypass graft using at least a portion of the enlarged (increased overall or lumen diameter or increased length) segment d of the accepting peripheral vein 30, either at the same time that the pump-conduit assembly is removed or at a subsequent time. Alternatively, other surgeries or procedures could be performed using the enlarged vein.

Figure 5A:
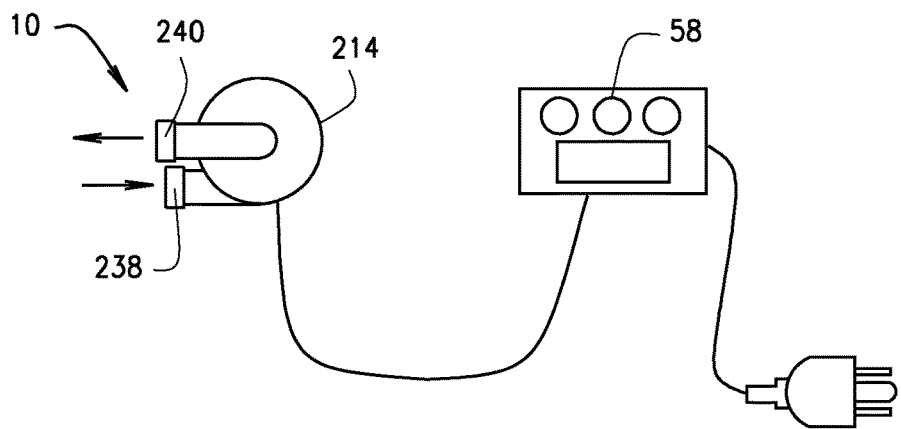
FIG. 5A is a schematic view of a pump-conduit assembly of a system and method in accordance with a fifth embodiment of the present invention.
Figure 5B:
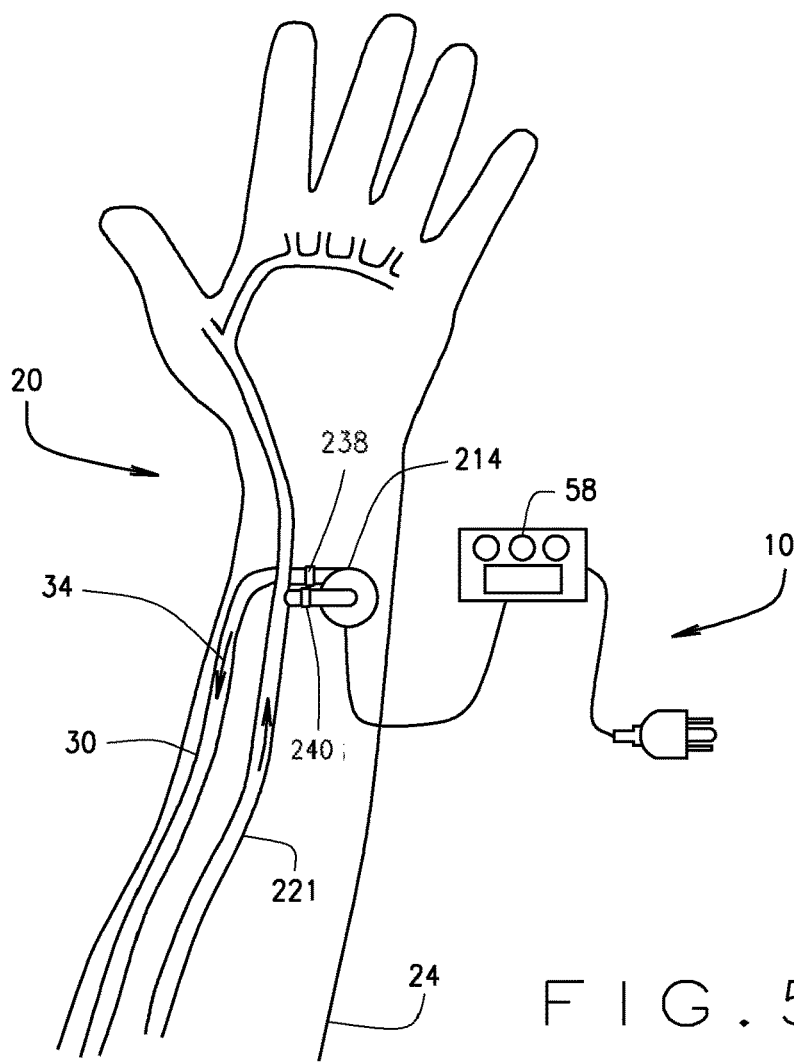
FIG. 5B is a schematic view of the pump-conduit assembly of FIG. 5A as applied to a circulatory system of a patient in accordance with the fifth embodiment of the present invention.

Referring to FIGS. 5A and 5B, a system 10 to increase the overall diameter of peripheral veins is illustrated as used for a patient 20. The system 10 draws oxygenated arterial blood from a patient's peripheral artery 221 and discharges that blood into the accepting peripheral vein 30 and is configured and operated to increase the blood speed and WSS in the accepting peripheral vein 30 for a period of time sufficient to cause a persistent increase in the diameter of the accepting peripheral vein 30 in, for example, an arm 24 or a leg 26. An embodiment of a system 10 in which a pump 214 is implanted in the arm 24 is illustrated. The pump 214 has an inlet 240 connected to an artery 221 in the arm 24 via anastomotic connection. The pump 214 also has an outlet 238 connected to the peripheral vein 30 via an anastomotic connection. The pump 214 is controlled and powered by the control unit 58. In operation, the pump 214 draws blood from the artery 221 and pumps the blood into the peripheral vein 30. This embodiment avoids the need for extended synthetic conduits and increases blood speed and WSS in both the peripheral vein 30 and the peripheral artery 221 resulting in, if operated for a sufficient period of time, simultaneous persistent increases in the overall diameter and lumen diameter of the vein 30 and the artery 221. Specifically, the pump 214 is implanted in the forearm 24 of the patient 20. Once the desired persistent increase in the overall diameter and lumen diameter has occurred in the accepting peripheral vein 30, the pump 214 can be removed and a surgical procedure can be performed to create a hemodialysis access site or bypass graft using at least a portion the enlarged artery 221 or vein 30, either at that time or during a subsequent operation.

In other embodiments, oxygenated arterial blood may be moved from a donating artery to an accepting location. Donating arteries may include, but are not limited to, a radial artery, ulnar artery, interosseous artery, brachial artery, anterior tibial artery, posterior tibial artery, peroneal artery, popliteal artery, profunda artery, superficial femoral artery, or femoral artery. Oxygenated blood may be moved from a donating artery to an accepting location passively based on an inherent pressure difference or actively by incorporating a pump into the system.

Figure 6:
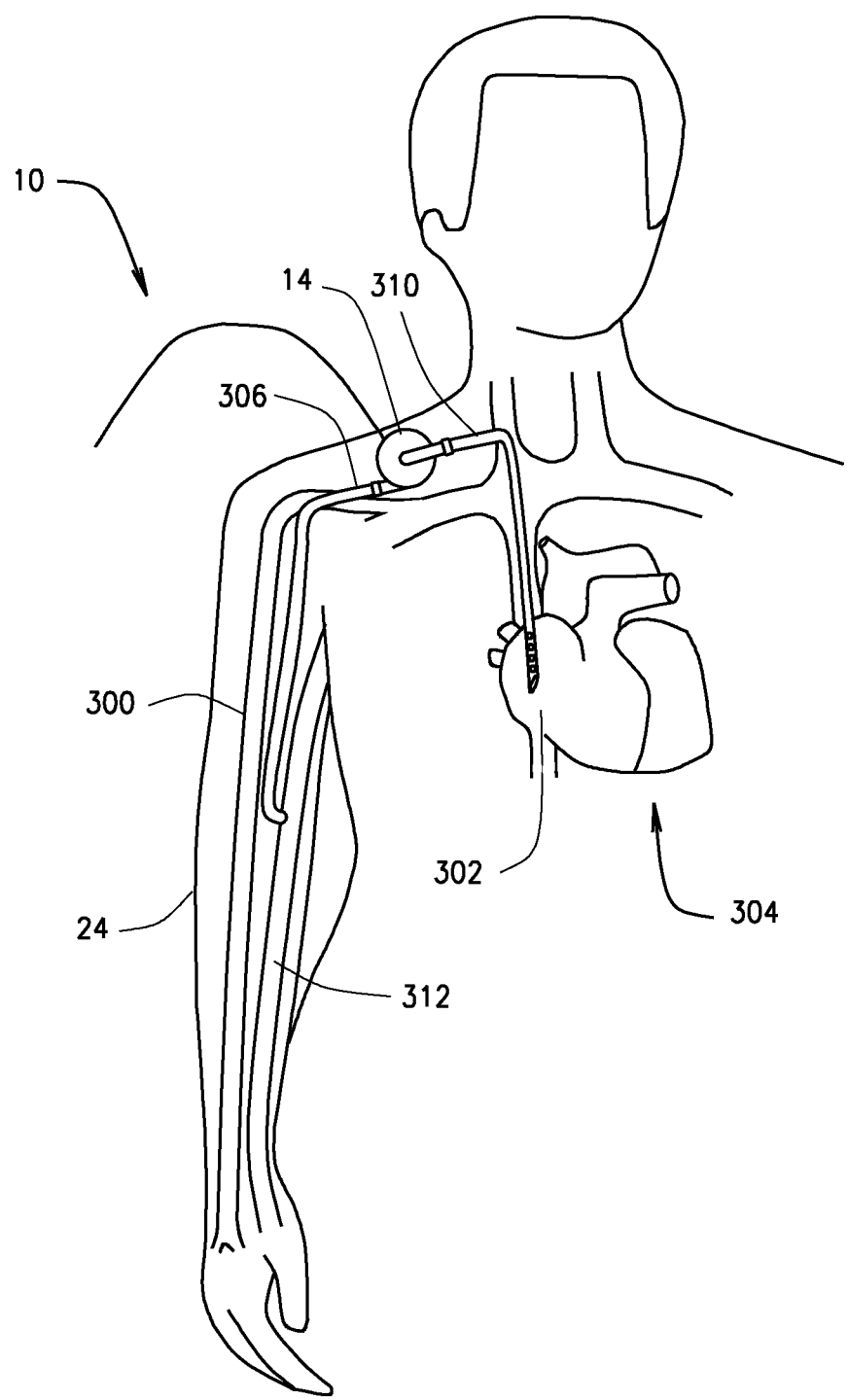
FIG. 6 is a schematic view of a pump-conduit assembly of a system and method in accordance with a sixth embodiment of the present invention.

FIG. 6 illustrates another embodiment for using the system 10 to increase the overall diameter and lumen diameter of a blood vessel. In this embodiment, the system 10 is configured to remove oxygenated blood from a donating artery 312 (in this case the brachial artery) and move the blood to the superior vena cava and right atrium 302 of the heart 304. As shown, an inflow conduit 306 is connected in fluid communication with the donating artery 312. In one embodiment, the connection may be made using a short ePTFE segment of the inflow conduit 306 that is used to secure the inflow conduit to the donating artery 312 while the remaining segment of the inflow conduit is made using polyurethane. In other embodiments, one or both segments of the inflow conduit 306 further comprise nitinol, such as for kink and compression resistance. As shown, one end of the outflow conduit 310 is connected to the pump 14 while the other end of the outflow conduit is fluidly connected to the superior vena cava and the right atrium 302 by an intravascular catheter portion. For the embodiment of FIG. 6, a pump 14 is used increase the rate at which blood is drawn from the donating artery 312 and discharged to the right atrium 302 of the heart 304 in order to achieve a desired elevated level of blood speed and elevated level of WSS in the donating artery 312. The pump is operated at a rate and for a time sufficient to result in a desired persistent increase in the overall diameter and lumen diameter of the donating artery, such as a 5% increase, 10% increase, a 25% increase, a 50% increase, or an increase of 100% or more from the starting diameter.

Figure 7:
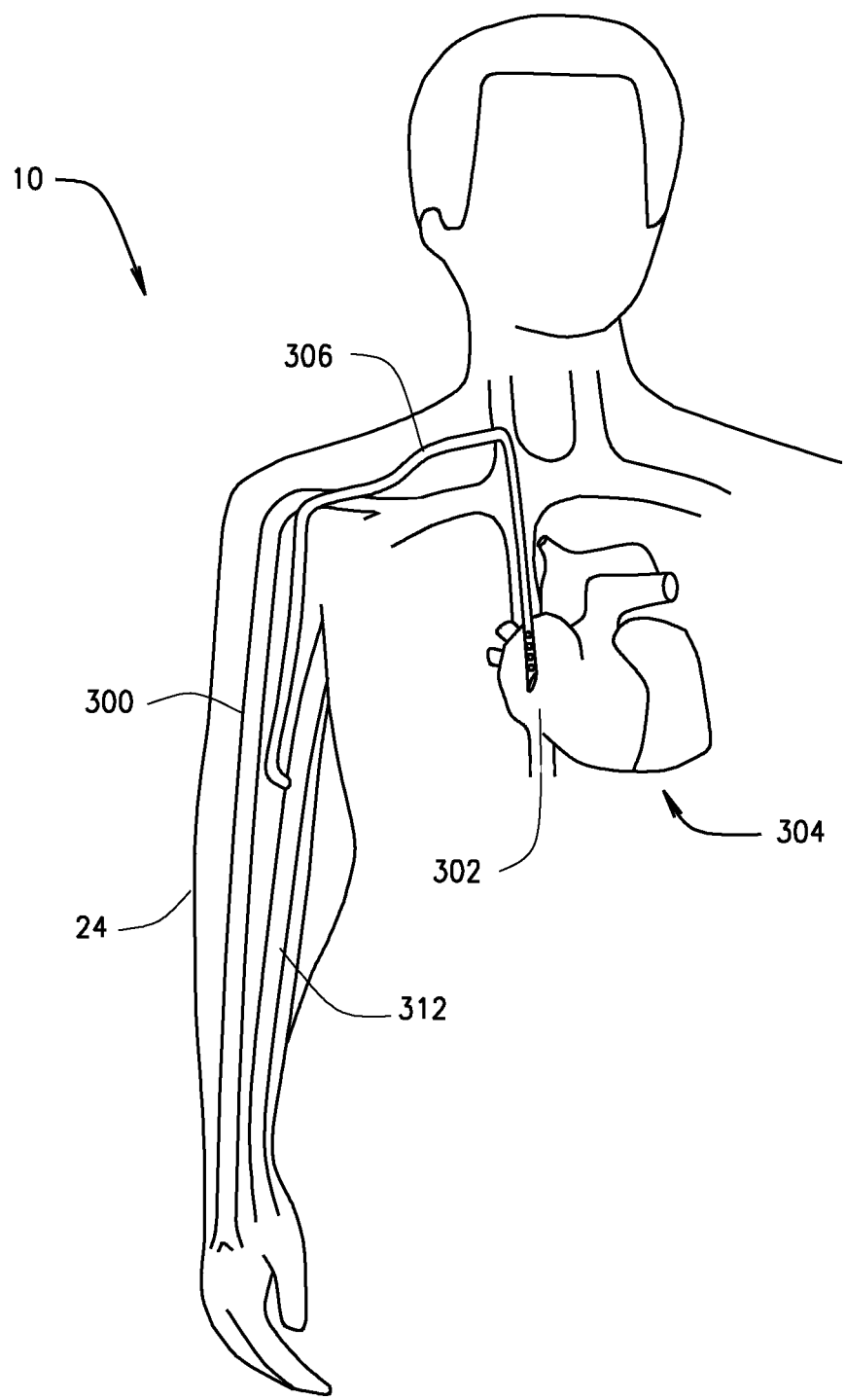
FIG. 7 is a schematic view of a pump-conduit assembly of a system and method in accordance with a seventh embodiment of the present invention.

FIG. 7 illustrates another embodiment for using the system 10 to increase the overall diameter and lumen diameter of a blood vessel. In this embodiment, the system 10 is configured to remove oxygenated blood from a donating artery 312 (in this case the brachial artery) and move the blood to the superior vena cava and right atrium 302 of the heart 304. As shown, in this embodiment there is one conduit inflow 306 that is connected at one end in fluid communication with the donating artery 312. In one embodiment, the connection to the donating artery 312 may be made using a short ePTFE segment of the conduit 306 that is used to secure the conduit to the donating artery 312 while the remaining segment of the conduit is made using polyurethane. In other embodiments, some or all of the conduit 306 further comprise nitinol, such as for kink and compression resistance. For the embodiment of FIG. 7, there is no pump and blood passively moves from the higher pressure donating artery 312 to the lower pressure superior vena cava and right atrium 302, and the conduit 306 is configured in length and lumen diameter to achieve a desired elevated level of blood speed and WSS in the donating artery 312. The conduit 306 remains in place for a time sufficient to result in a desired persistent increase in the overall diameter and lumen diameter of the donating artery 300, such as a 5% increase, 10% increase, a 25% increase, a 50% increase, or an increase of 100% or more from the starting diameter.

In one embodiment, a method for using the system 10, as shown in FIG. 7, involves a single conduit and includes accessing the artery 312. Connecting one end of the conduit 306 catheter to the artery 312 and another end of the conduit to an accepting location (e.g. the right atrium 302 of the heart 304), such that at least a portion of the blood flowing within the artery is directed away from the artery and to the accepting location. In this method, the blood moves passively from the higher pressure artery 312 to the lower pressure right atrium 302 without requiring a pump. After a period of time, the overall diameter and lumen diameter of the artery 312 increases. Then, the conduit 306 is disconnected from the artery 312 and the right atrium 302 and a portion of the artery is prepared for use as a hemodialysis access site, a bypass graft, or in another surgery where an artery is used or needed.

Figure 8:
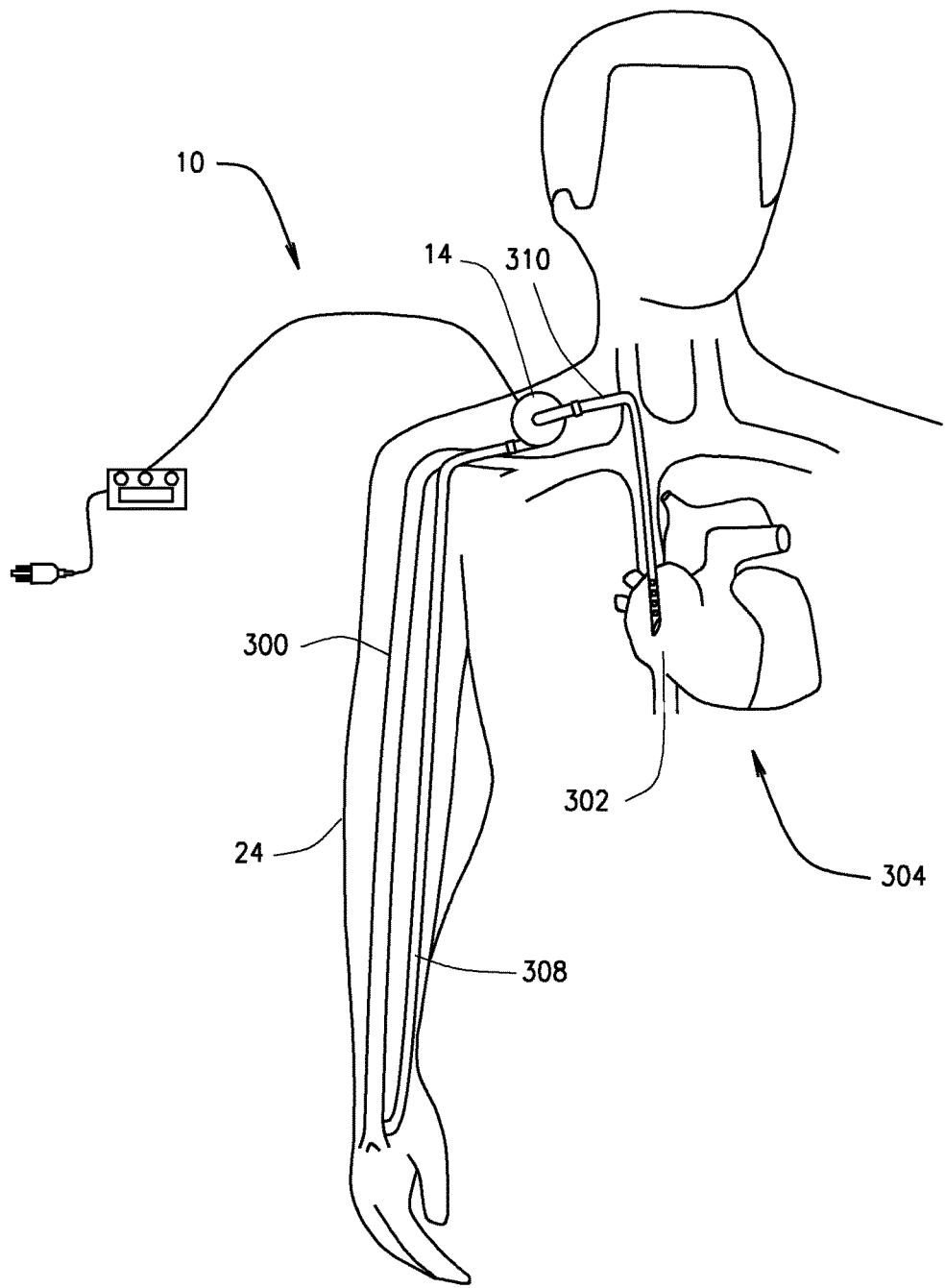
FIG. 8 is a schematic view of a pump-conduit assembly of a system and method in accordance with an eighth embodiment of the present invention.

FIG. 8 illustrates another embodiment for using the system 10 to increase the overall diameter and lumen diameter of a target blood vessel. In this embodiment, the system 10 is configured to remove deoxygenated blood from a donating vein 300 and move the blood to the superior vena cava and right atrium 302 of the heart 304. As shown, an inflow conduit 306 is connected in fluid communication with the donating vein 300, in this case the cephalic vein. In one embodiment, the connection may be made using a short ePTFE segment of the inflow conduit 306 that is used to secure the inflow conduit 308 to the donating vein 300 while the remaining segment of the inflow conduit is made using polyurethane. In other embodiments, at least a portion of the inflow or outflow conduit comprises nitinol for kink and compression resistance. As shown, one end of the outflow conduit 310 is connected to the pump 14 while the other end of the outflow conduit is fluidly connected to the right atrium 302 of the heart 304 by an intravascular portion. For the embodiment of FIG. 8, a pump 14 is used increase the rate at which blood is drawn from the donating vein 300 and discharged into the right atrium 302 of the heart 304 in order to achieve a desired elevated level of blood speed and elevated level of WSS in the donating vein 300. The pump is operated at a rate and for a time sufficient to result in a desired persistent increase in the overall diameter and lumen diameter of the donating vein 300, such as a 5% increase, 10% increase, a 25% increase, a 50% increase, or an increase of 100% or more from the starting diameter. In a further embodiment, one or more venous valves between the junction of the inflow conduit 308 and the donating vein 300, and the right atrium 302 may be rendered incompetent or more incompetent (using any of the methods available to one skilled in the art) to allow blood to flow in a retrograde fashion in the donating vein 300 (away from the heart) and then into the inflow conduit 308.

In other embodiments, such as when a peripheral artery is the donating vessel and a peripheral vein is the accepting vein, the blood is pumped into the accepting peripheral vein with a pulsatility that is reduced when compared with the pulsatility of blood in a peripheral artery. For example, the mean pulse pressure in the accepting peripheral vein adjacent to the connection with the outflow conduit is <40 mmHg, <30 mmHg, <20 mmHg, <10 mmHg, or preferably <5 mmHg with the pump operating. In order to reduce pulsatility and/or provide low-pulsatile flow, a number of pulsatility dampening techniques may be used. By way of example, and not limitation, such techniques include tuning the head-flow characteristics of a blood pump, adding an elastic reservoir or Windkessel segment to the inflow or outflow conduits, adding compliance to the inflow or outflow conduits, modulating the pump speed, such as a modulation that increases pump speed during diastole and decreases pump speed during systole, or adding counterpulsation to the inflow or outflow conduits or the pump.

Referring to FIG. 9, a schematic of an embodiment of the pump system 10 is illustrated. The control unit 58 is connected to the pump 14 and is configured to control the speed of the pump 14 and collect information on the function of the pump system 10. The control unit 58 may be implanted in the patient 20, may remain external to the patient 20, or may have implanted and external portions. A power source is embodied in a power unit 60 and is connected to the control unit 58 and the pump 14. The power unit 60 provides energy to the pump 14 and the control unit 58 for routine operation. The power unit 60 may be implanted in the patient 20, may remain external to the patient 20, or may have implanted and external portions. The power unit 60 may include a battery 61. The battery 61 is preferably rechargeable and in this embodiment is recharged via an electrical connector 69 to a power source. Such rechargeable batteries could also be recharged using lead wires or via transcutaneous energy transmission, such as when implanted. In another embodiment, rechargeable batteries that have been depleted could be recharged in a charging station connected to a wall outlet and then exchanged with batteries of the pump system 10 that have been depleted. Optionally, the electrical connector 69 may deliver electrical power to the power unit 60 without the aid of the battery 61. It will be apparent to one of ordinary skill in the art from this disclosure that the control unit 58 can be configured to utilize alternative power and control systems.

Sensors 66 and 67 may be incorporated into the vascular system, conduits 16 and 18, the pump 14, or the control unit 58. The sensors 66 and 67 are connected to the control unit 58 via cable 68 or can wirelessly communicate with the control unit 58. Without being limited by the provided examples, the sensors 66 and 67 can measure various pump, conduit, control unit, or system parameters, including the power or current necessary to operate the pump under certain operating conditions, a blood speed, a rate of blood flow, a resistance to blood flow from a donating vessel or into a peripheral accepting vein, a blood pressure or pulse pressure, a pulsatility index, and combinations thereof and may send signals to the pump or the control unit 58. The control unit 58 (also referred to as the controller) may use these measurements to determine (or estimate) any one or more of: lumen diameter of adjacent target vessels in fluid communication with conduits, resistance to flow, or WSS in target blood vessels, including an accepting vein, a donating vein, or a donating artery and may send signals to pump to alter pump speed, impeller speed, conduit blood pressure, or other pump system parameters. For example, as the overall diameter and lumen diameter of the peripheral vein 30 receiving the pumped blood increases, blood speed and WSS in the peripheral vein 30 decreases along with resistance to blood flow 34 from the outflow conduit 18. In order to maintain the desired blood speed and WSS, the pump speed may be adjusted as the overall diameter and lumen diameter of the peripheral accepting vein 30 increases over time.

As mentioned previously, the control unit may rely on a measurement, including an internal measurement of the electrical current to the motor 44 as a basis for estimating blood flow, blood speed, intraluminal pressure, or resistance to flow. The control unit 58 may also include manual controls to adjust pump speed, impeller speed, or other pumping parameters.

The control unit 58 is operatively connected to the pump-conduit assembly 12. Specifically, the control unit 58 is operatively connected to the pump 14 by one or more cables 62. Utilizing the power unit 60, the control unit 58 preferably supplies pump motor control current, such as pulse width modulated motor control current to the pump 14 via cable 62. The control unit 58 can also receive data and information from the pump 14. The control unit 58 further includes a communication unit 64 that is configured to collect data and information, and communicate this, as for example by telemetric transmission. Furthermore, the communication unit 64 is configured to receive instructions or data for reprogramming the control unit 58. Therefore, the communication unit 64 is configured to receive instructions or data that subsequently is used to change the functioning of the pump 14.

The present invention provides a monitoring system, constituted by the control unit 58 and sensors 66 and 67, to adjust the operation of the pump to maintain the desired blood velocity and WSS in the target vessel as the overall diameter and lumen diameter of the target vessel increase over time.

Preferably, the pump 14 is configured to provide a blood flow 34 in a range from about 50-2500 mL/min. The pump 14 is configured to increase the mean WSS in a target vein to a range of between 0.76 Pa and 23 Pa, preferably to a range between 2.5 Pa and 10 Pa. The pump 14 is configured to increase the mean WS S in a target artery to a range of between 1.5 Pa and 23 Pa, preferably to a range between 2.5 Pa and 10 Pa. The pump 14 is configured to maintain the desired level of blood flow, mean blood speed, and mean WSS in the target vein or artery for a period of about 7-84 days, for example, and preferably about 7-42 days, for example. In certain situations where a large persistent increase in the overall diameter and lumen diameter of a vein is desired or where a persistent increase in the overall diameter and lumen diameter of a vein occurs slowly, the pump 14 is configured to maintain the desired level of blood flow and WSS in the accepting peripheral vein 30 for longer than 84 days.

The pump-conduit assembly 12 can be implanted on the right side of the patient 20, or can be implanted on the left side, as need be. The lengths of the conduits 16 and 18 can be adjusted for the desired placement. Specifically for FIGS. 1B and 1C, the first end 46 of the inflow conduit 16 is fluidly connected to the right internal jugular vein 29 and the first end 52 of the outflow conduit 18 is fluidly connected to the cephalic vein 30 in the right forearm near the wrist. Specifically for FIGS. 2B and 2C, the first end 46 of the inflow conduit 16 is fluidly connected to the superior vena cava 27 and the first end 52 of the outflow conduit 18 is fluidly connected to the cephalic vein 30 in the right forearm 24 near the wrist. After connection, pumping is started. That is, the control unit 58 begins to operate the motor 44. The pump 14 pumps blood 34 through the outlet conduit 18 and into the peripheral vein 30. The control unit 58 adjusts pumping over the course of time by utilizing data provided by the sensors 66 and 67. FIGS. 1-4 illustrate examples in which the system 10 pumps deoxygenated blood. FIG. 5 illustrates an example in which the system 10 pumps oxygenated blood. In some embodiments, the blood is pumped into the accepting vein with a pulsatility that is reduced when compared with the pulsatility of blood in a peripheral artery. For example, the mean pulse pressure in the accepting vein is <40 mmHg, <30 mmHg, <20 mmHg, <10 mmHg, or preferably <5 mmHg with the pump operating and delivering blood into the peripheral vein. In other embodiments, the blood is pumped into the accepting vein with a pulsatility that is equal to or increased when compared with the pulsatility of blood in a peripheral artery. For these embodiments, the mean pulse pressure in the accepting vein adjacent to the connection with the outflow conduit is ≥40 mmHg with the pump operating.

In one specific embodiment illustrated in FIGS. 1B and 1C, the donating vein 29 is a jugular vein 21, preferentially an internal jugular vein 21. The internal jugular vein 21 is particularly useful as a donating vein 29 due to the absence of valves between the internal jugular vein 21 and the right atrium 31, which would allow the synthetic inflow conduit 16 to draw a large volume of deoxygenated blood per unit time, including drawing blood that is flowing in a retrograde manner in a portion of the jugular vein. The inflow conduit 18 is fluidly connected to the internal jugular vein 21 of the patient 20. Deoxygenated blood is removed from the internal jugular vein 21 and pumped into the peripheral accepting vein 30 in the arm 24 resulting in an increase in the speed of blood 34 and WSS in the peripheral accepting vein 30. In some embodiments, the blood is pumped into the accepting vein with a pulsatility that is reduced when compared with the pulsatility of blood in a peripheral artery. For example, the mean pulse pressure in the accepting vein adjacent to the connection with the outflow conduit is <40 mmHg, <30 mmHg, <20 mmHg, <10 mmHg, or preferably <5 mmHg with the pump operating.

As noted previously, FIG. 5B illustrates an example in which the system 10 draws and discharges oxygenated blood. The inflow conduit 240 is fluidly connected to the radial artery 221 of the patient 20 and the outflow conduit 238 is fluidly connected to the cephalic vein, both using an anastomotic connection. Thus, oxygenated blood is removed from the radial artery 221 and pumped into the cephalic vein 30 in the arm 24 in a manner that results in an increased blood speed and WSS in the cephalic vein for a sufficient period of time to cause a persistent increase in the overall diameter and lumen diameter of the accepting peripheral vein 30. In some embodiments, the blood is pumped into the accepting vein 30 with a pulsatility that is reduced when compared with the pulsatility of blood in a peripheral artery. For example, the mean pulse pressure in the accepting vein adjacent to the connection with the outflow conduit is <40 mmHg, <30 mmHg, <20 mmHg, <10 mmHg, or preferably <5 mmHg with the pump operating and delivering blood into the peripheral accepting vein.

Referring to FIGS. 10-14, various embodiments of the method 100 increase the overall diameter and the lumen diameter of a peripheral accepting vein, peripheral donating artery, or peripheral donating vein.

Figure 10:
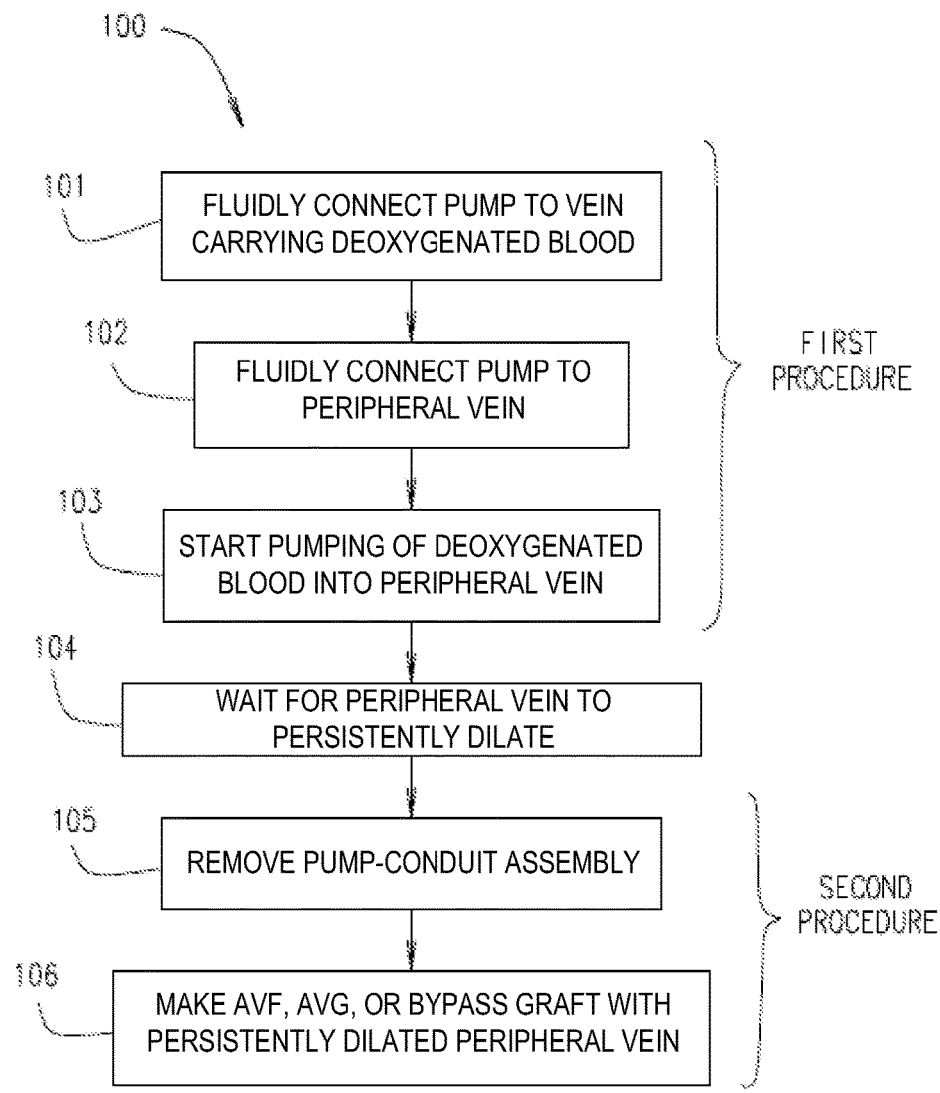
FIG. 10 is a flow chart of a method in accordance with the first and third embodiments of the present invention.

As shown in FIG. 10, in an embodiment of the method 100, a physician or surgeon performs a procedure to access a vein and connects a pump to establish fluid communication with a vein carrying deoxygenated blood at step 101. At step 102, the pump is connected to a peripheral vein. In this embodiment, the pump-conduit assembly 12 is implanted in the neck, chest, or arm 24 of the patient 20. In another embodiment, wherein the peripheral vein 30 is the greater saphenous vein 30, the pump-conduit assembly 12 is implanted in the leg 26, pelvis, or abdomen. In one example, the physician fluidly connects the first end 46 of the pump-conduit assembly 12 to the donating vein 29, (in this case the proximal greater saphenous vein) and the second end of the pump-conduit assembly 12 to the peripheral accepting vein 30, (in this case the distal greater saphenous vein) utilizing a tunneling procedure (as necessary) to connect the two locations subcutaneously. At step 103, the deoxygenated blood is pumped into the peripheral accepting vein. At step 104, the pumping continues for a period of time, while the physician waits for the overall diameter and lumen diameter of the peripheral accepting vein to persistently increase. In one embodiment, after the pump is turned on to start the pumping of deoxygenated blood, the skin incisions are closed, as necessary. In another embodiment, portions of the synthetic conduits 16 and 18 and the pump 14 are extracorporeally located. In this embodiment, the pump 14 is then started and controlled via the control unit 58 to pump the deoxygenated blood through the pump-conduit assembly 12 and into the peripheral accepting vein 30 in a manner that increases the blood speed and WSS in the peripheral vein 30. The operation of the pump system and other parameters mentioned previously are monitored periodically and the control unit 58 is used to adjust the operating parameters of the pump 14, in response to changes (such as an increased overall diameter or lumen diameter of the peripheral accepting vein 30. With periodic adjustments, as necessary, the pump continues to operate for an amount of time sufficient to result in the persistent increase in the overall diameter, lumen diameter, or length of the peripheral vein 30. In a subsequent procedure, the pump-conduit assembly 12 is disconnected from the patient and the pump system is removed at step 105. At step 106, the peripheral vein with the persistently increased overall diameter and lumen diameter 30 is used to create an AVF, AVG, bypass graft, or other surgery or procedure requiring a vein, as determined by one skilled in the art.

Figure 11:
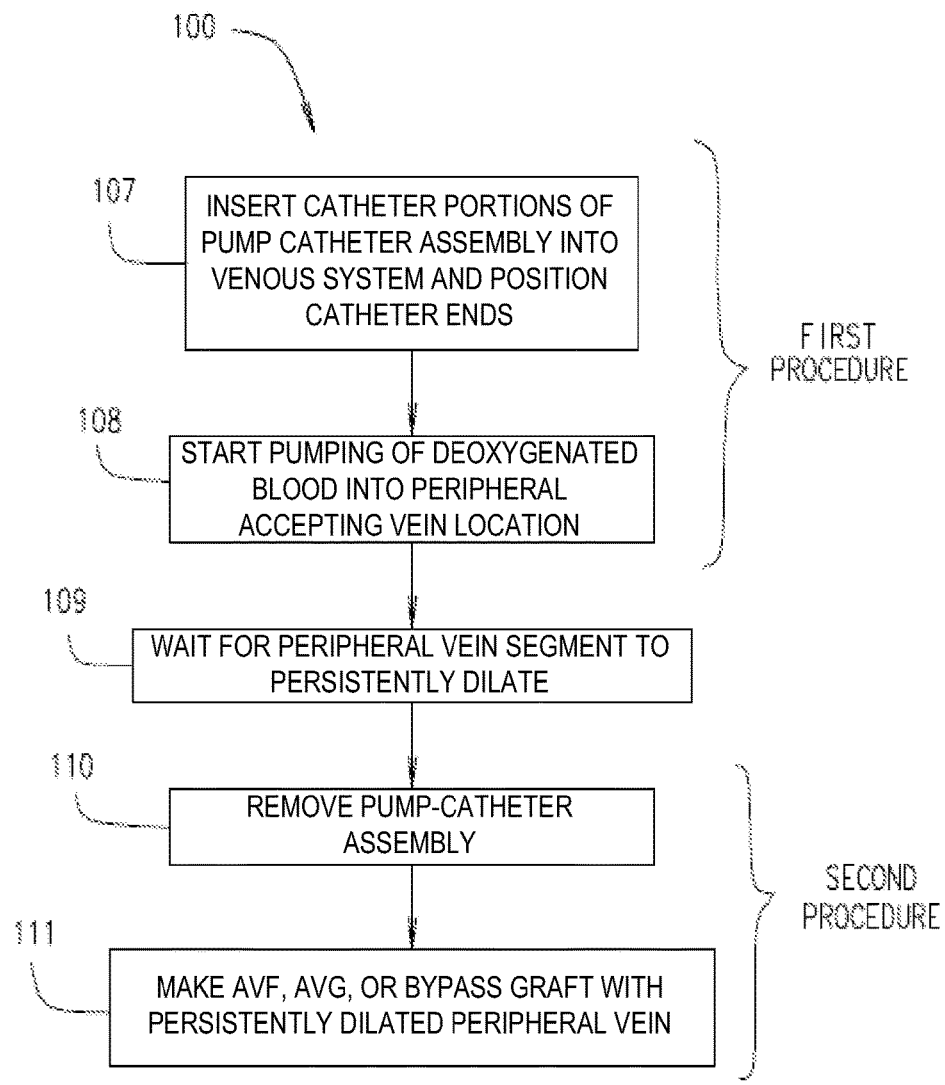
FIG. 11 is a flow chart of a method in accordance with the second and fourth embodiments of the present invention.

As shown in FIG. 11, in another embodiment of the method 100, the physician or surgeon inserts the inflow catheter conduit 55 of the pump-catheter assembly into the venous system and positions it in a donating vessel location. The physician or surgeon then inserts the outflow catheter conduit 56 of the pump-catheter assembly into the venous system and positions it in a peripheral accepting vein 30 location at step 107. At step 108, the pump is operated to pump deoxygenated blood from the donating vessel location 29 to the peripheral accepting vein location 30. The physician then waits for the overall diameter and lumen diameter of the peripheral vein segment d to increase to the desired amount at step 109. The pump-catheter assembly is then removed at step 110 and the peripheral accepting vein segment with a persistent increase in the overall diameter and lumen diameter is used to create an AVF, AVG, or bypass graft, or other surgery or procedure requiring a vein, as determined by one skilled in the art at step 111.

Figure 12:
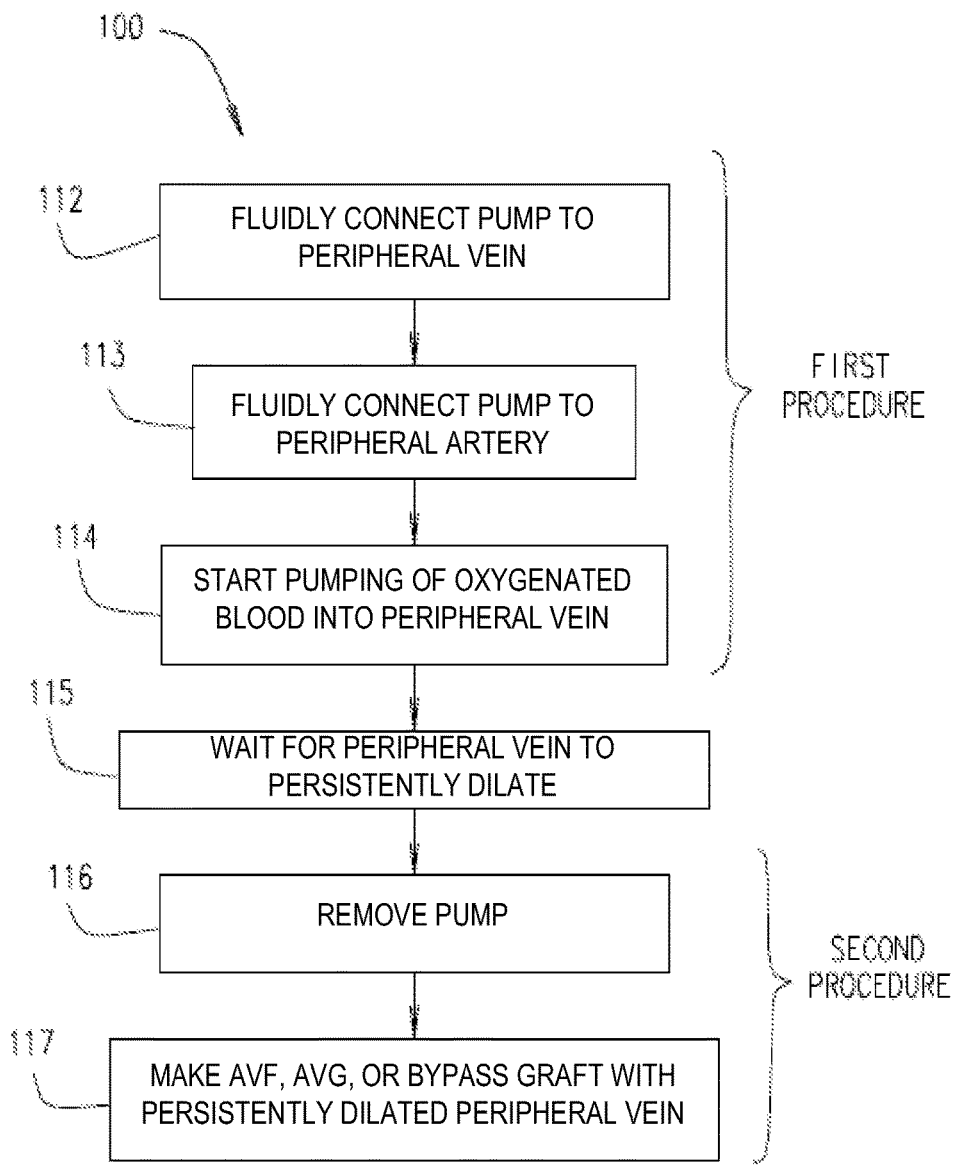
FIG. 12 is a flow chart of a method in accordance with the fifth embodiment of the present invention.

As shown in FIG. 12 in another embodiment of the method 100, a physician or surgeon performs a procedure to access a peripheral vein 30 and connects a pump (directly or via an outflow conduit) to establish fluid communication with the peripheral vein 30 at step 112. The pump is fluidly connected to a peripheral artery 221 (directly or via an inflow conduit) at step 113. The pump is operated at step 114 to pump oxygenated blood from the donating peripheral artery 221 to the accepting peripheral vein 30. At step 115, the pumping continues for a period of time, while the physician waits for the overall diameter and lumen diameter of the accepting peripheral vein to persistently increase to the desired amount. At step 116, the blood pump system is removed and at step 117, the peripheral accepting vein with a persistent increase in the overall diameter and lumen diameter is used to create an AVF, AVG, or bypass graft, or other surgery or procedure requiring a vein, as determined by one skilled in the art.

Figure 13:
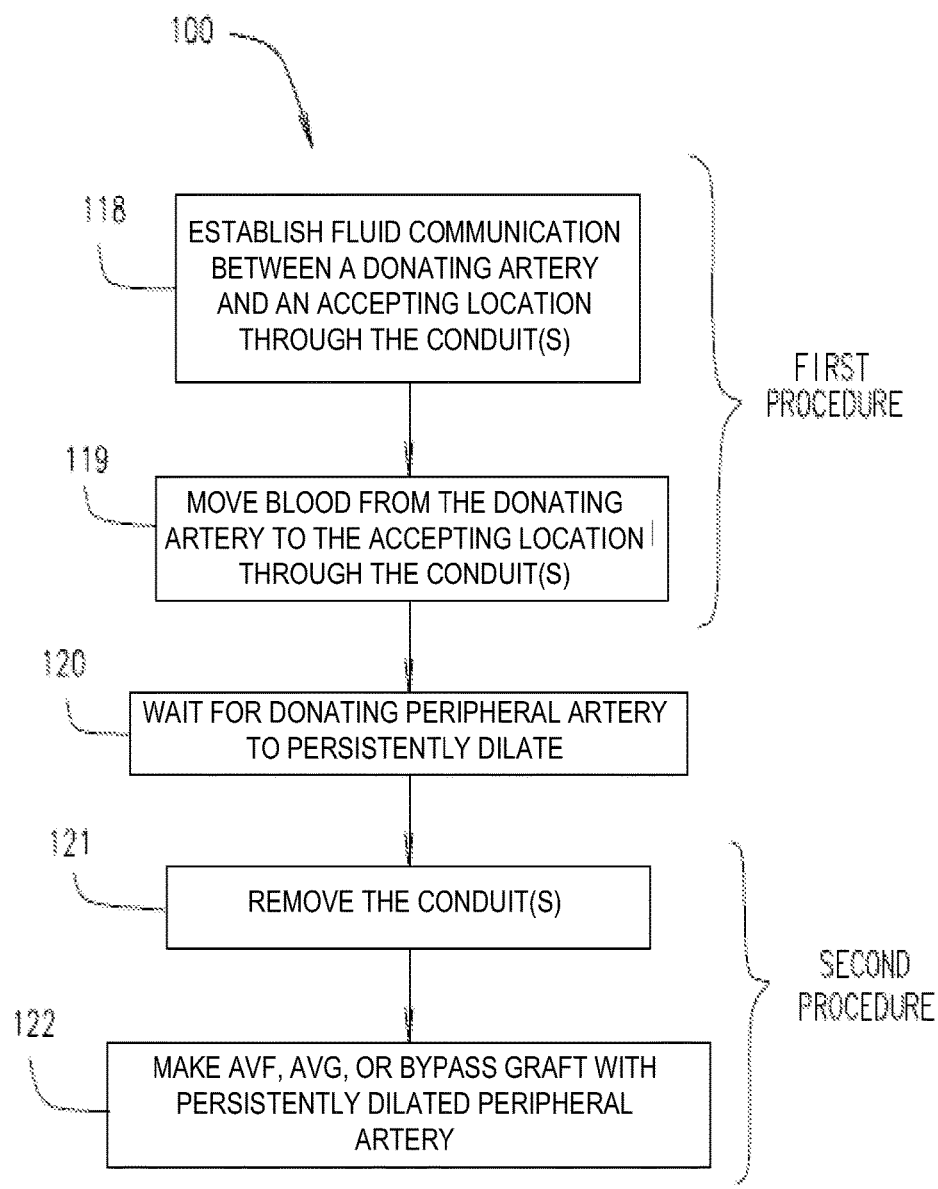
FIG. 13 is a flow chart of a method in accordance with the sixth and seventh embodiment of the present invention.

As shown in FIG. 13 in another embodiment of the method 100, at step 118 a physician or surgeon performs a procedure to access a peripheral donating artery and uses one or more conduits to establish a fluid communication with an accepting location such as the superior vena cava or the right atrium. At step 119, blood moves from the donating artery to the accepting location, which can be accomplished in a passive manner without a pump or in an active manner with the assistance of a pump. At step 120, blood is moved from the donating artery to the accepting location for a period of time, while the physician waits for the overall diameter and lumen diameter of the peripheral donating artery to persistently increase to the desired amount. At step 121, the conduit(s) are removed. In some embodiments, a pump is removed at step 121 as well. At step 122, the peripheral donating artery with a persistent increase in the overall diameter and lumen diameter is used to create an AVF, AVG, or bypass graft, or other surgery or procedure requiring an artery, as determined by one skilled in the art.

Figure 14:
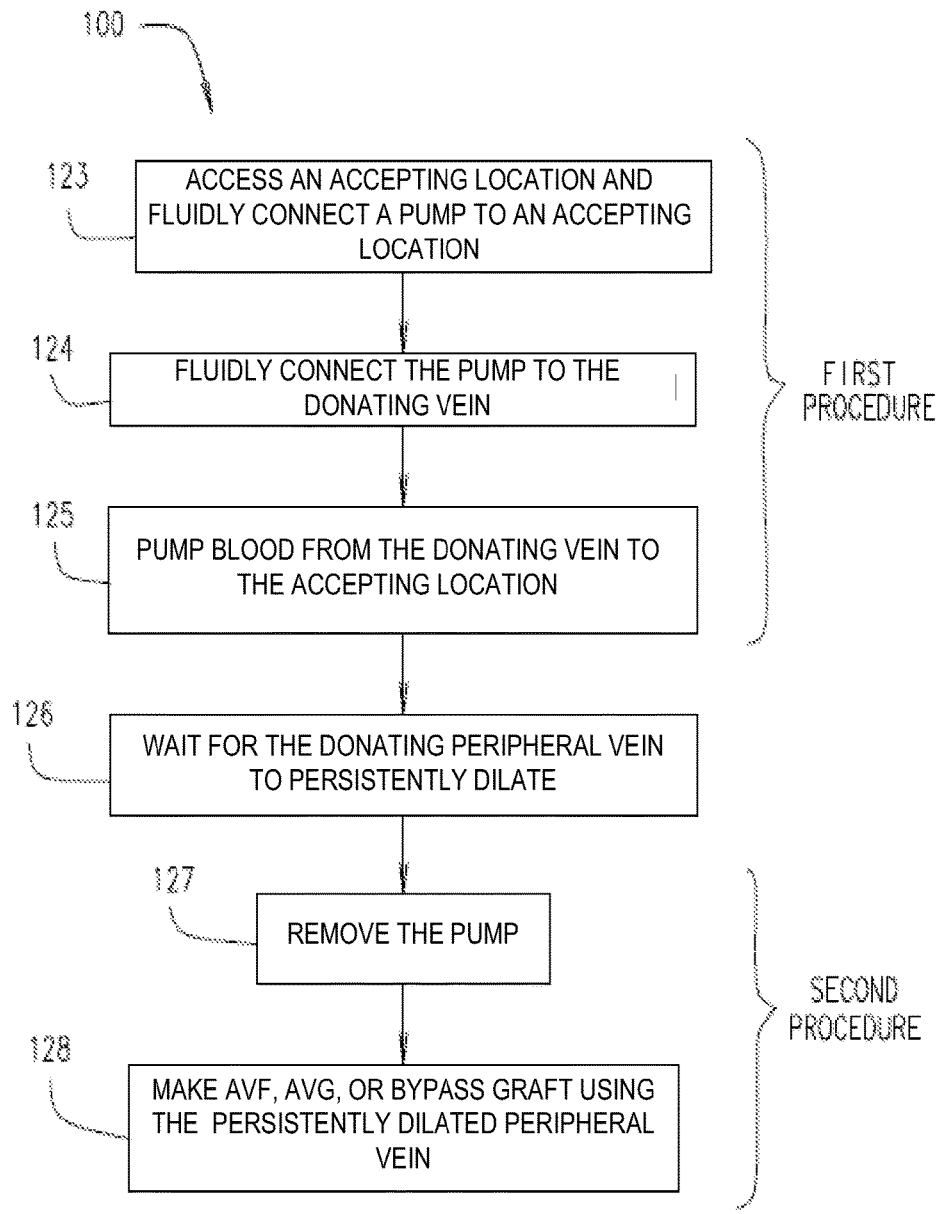
FIG. 14 is a flow chart of a method in accordance with the eighth embodiment of the present invention.

As shown in FIG. 14 in another embodiment of the method 100, a physician or surgeon performs a procedure to fluidly access an accepting location in the vascular system (such as the superior vena cava or the right atrium) and fluidly connects a pump (directly or via an inflow conduit) to the accepting location at step 123. Then the physician or surgeon establishes a fluid communication between a peripheral donating vein and the pump (directly or via an outflow conduit) at step 124. The pump is operated at step 125 to pump deoxygenated blood from the peripheral donating vein to the accepting location. At step 126, the pumping continues for a period of time, while the physician waits for the overall diameter and lumen diameter of the peripheral donating vein to persistently increase. At step 127, the pump system is removed and at step 128, the donating vein with a persistent increase in the overall diameter and lumen diameter is used to create an AVF, AVG, or bypass graft, or other surgery or procedure requiring a vein, as determined by one skilled in the art.

In various embodiments, the method 100 and/or the system 10 may be used for periodic and/or intermittent sessions, as opposed to continuous treatment. Typically, hemodialysis treatments that may last from 3 to 5 hours are given in a dialysis facility up to 3 times a week. Various embodiments of the system 10 and method 100 may be used to provide blood pumping treatments on a similar schedule over a 4 to 6 week period. The treatments may be performed in any suitable location, including in an outpatient setting.

In one embodiment, the blood pumping treatment is done intermittently in conjunction with hemodialysis treatments. In this embodiment, a low-flow pump, a standard in-dwelling hemodialysis catheter functioning as an inflow catheter, and a minimally traumatic needle or catheter placed in the peripheral vein to function as an outflow catheter may be used. A number of continuous flow blood pumps operated from a bedside console (e.g. catheter-based VADs and pediatric cardiopulmonary bypass or extracorporeal membrane oxygenation pumps may be easily adapted for use with the method 100.

In various embodiments where the blood pumping occurs through periodic intermittent pumping sessions, the access to the blood vessels may also occur through one or more ports or surgically created access sites. By way of example and not limitation, the access may be achieved for inflow through a venous needle, a peripherally inserted central venous catheter, a tunneled or non-tunneled central venous catheter, or a subcutaneously implantable central venous catheter with a port, an arterial needle, or an arterial catheter. By way of example and not limitation, the access may be achieved for outflow through a venous needle or a peripheral venous catheter.

In another embodiment of the system 10, a low-flow pump is used to increase mean WSS and mean blood speed in a blood vessel. The low-flow pump has an inlet conduit fluidly connected to a blood vessel or location in the cardiovascular system such as the right atrium and an outlet conduit fluidly connected to a vein and pumps blood from the blood vessel or location in the cardiovascular system to the vein for a period between about 7 days and 84 days. The low-flow pump pumps blood such that the mean wall shear stress of the vein ranges between about 0.076 Pa to about 23 Pa. The low-flow pump also includes an adjustment device. The adjustment device may be in communication with a software-based automatic adjustment system or the adjustment device may have manual controls. The inlet conduit and the outlet conduit may range in length from about 0.5 centimeters to about 110 centimeters, and have a total range in length from 4 and 220 centimeters.

The present invention also relates to a method of assembling and operating a blood pump system, including various embodiments of the pump-conduit system 10. The method includes attaching a first conduit in fluid communication with the pump-conduit system 10 to an artery and attaching a second conduit in fluid communication with the pump-conduit system to a vein. The pump-conduit system 10 is then activated to pump blood between the artery and the vein.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having", and their derivatives. The terms of degree such as "substantially", "about" and "approximate" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. For example, the size, shape, location, or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature that is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for limiting the invention as defined by the appended claims and their equivalents.

What is claimed is:

1. A method for creating an arteriovenous fistula or an arteriovenous graft in a human patient, the method comprising:
    fluidly connecting one end of a pump-conduit assembly to the donating vein or location;
    fluidly connecting another end of the pump-conduit assembly to an accepting vein; and,
    pumping venous blood from the donating vein or location into the accepting vein, wherein: the pumping of blood results in a mean wall shear stress in the accepting vein of greater than or equal to 0.76 Pa;
    the pumping of blood results in a mean pulse pressure in the accepting vein of less than 40 mmHg; and
    the pumping of blood results in an increase in the lumen diameter and overall diameter of the accepting vein which persists after pumping has ceased; and,
    creating the arteriovenous fistula or arteriovenous graft in the patient using at least a portion of the accepting vein with the persistently-increased lumen diameter and overall diameter.

2. The method of claim 1, wherein the pump-conduit assembly pumps deoxygenated blood.

3. The method of claim 2, wherein the pumping of blood results in an increase in the length of the accepting vein, which persists after pumping has ceased.

4. The method of claim 2 further comprising: determining the overall diameter or lumen diameter of the accepting vein and blood flow through the accepting vein after pumping the blood; and, changing a speed of a pump portion of the pump-conduit assembly in order to maintain a desired wall mean shear stress or a desired mean blood speed in the accepting vein.

5. The method of claim 2, wherein a wall shear stress in the donating vein is greater than or equal to 0.76 Pa when the pump-conduit assembly is in operation.

6. The method of claim 2, wherein a mean speed of the blood in the donating vein is between 15 cm/s and 100 cm/s when the pump-conduit assembly is in operation.

7. The method of claim 1, wherein the pump-conduit assembly pumps blood at a rate between 50 ml/min and 2500 ml/min.

8. The method of claim 7, wherein the pumping of blood results in an increase in the length of the accepting vein, which persists after pumping has ceased.

9. The method of claim 7 further comprising: determining the overall diameter or lumen diameter of the accepting vein and blood flow through the accepting vein after pumping the blood; and, changing a speed of a pump portion of the pump-conduit assembly in order to maintain a desired wall mean shear stress or a desired mean blood speed in the accepting vein.

10. The method of claim 7, wherein a wall shear stress in the donating vein is greater than or equal to 0.76 Pa when the pump-conduit assembly is in operation.

11. The method of claim 7, wherein a mean speed of the blood in the donating vein is between 15 cm/s and 100 cm/s when the pump-conduit assembly is in operation.

12. The method of claim 1, wherein a wall shear stress in the donating vein is greater than or equal to 0.76 Pa when the pump-conduit assembly is in operation.

13. The method of claim 1, wherein a mean wall shear stress in the accepting vein is between 0.76 Pa and 23 Pa when the pump-conduit assembly is in operation.

14. The method of claim 1, wherein a mean wall shear stress in the accepting vein is between 1.5 Pa and 23 Pa when the pump-conduit assembly is in operation.

15. The method of claim 1, wherein a mean wall shear stress in the donating vein is between 2.5 Pa and 10 Pa when the pump-conduit assembly is in operation.

16. The method of claim 1, wherein a mean speed of the blood in the donating vein is between 15 cm/s and 100 cm/s when the pump-conduit assembly is in operation.

17. The method of claim 1, wherein a mean speed of the blood in the accepting vein is between 10 cm/s and 120 cm/s when the pump-conduit assembly is in operation.

18. The method of claim 1, wherein a mean speed of the blood in the accepting vein is between 25 cm/s and 120 cm/s when the pump-conduit assembly is in operation.

19. The method of claim 1, wherein blood is pumped through the pump-conduit assembly for period at least one day.

20. The method of claim 1 further comprising: determining the overall diameter or lumen diameter of the accepting vein and blood flow through the accepting vein after pumping the blood; and, changing a speed of a pump portion of the pump-conduit assembly in order to maintain a desired wall mean shear stress or a desired mean blood speed in the accepting vein.

21. The method of claim 1, wherein blood is pumped through the pump-conduit assembly until the lumen diameter or overall diameter of the accepting vein is increased by 5 percent or more from a starting diameter.

22. The method of claim 1, wherein the donating vein or location is selected from a group consisting of a right atrium, a superior vena cava, an inferior vena cava, a brachiocephalic vein, a jugular vein, a subclavian vein, an axillary vein, a common iliac vein, an external iliac vein, or a femoral vein.

23. The method of claim 1, wherein the accepting vein is selected from a group consisting of a cephalic vein, a median cephalic vein, an ulnar vein, a radial vein, a median vein, an antecubital vein, a basilic vein, a median basilic vein, a brachial vein, a lesser saphenous vein, a greater saphenous vein, or a femoral vein.

24. The method of claim 1, wherein the pumping of blood results in a mean pulse pressure in the segment of accepting vein adjacent to the fluid connection with the second conduit of less than 30 mmHg when the pump-conduit assembly is in operation.

25. The method of claim 1, wherein a pump portion of the pump-conduit assembly is implanted in the patient.

26. The method of claim 1, wherein a pump portion of the pump-conduit assembly remains extracorporeal to the patient.

27. The method of claim 1, wherein the persistently-increased lumen diameter or overall diameter of the accepting vein is at least 2.5 mm or 4.0 mm.

28. The method of claim 1, wherein the pump is a rotary blood pump.

29. The method of claim 28, wherein the rotary blood pump is a centrifugal pump.

30. The method of claim 1, wherein the pump of the pump-conduit assembly is configured with at least one contact bearing.

31. The method of claim 1, wherein the pump of the pump-conduit assembly is driven by an electric motor.

32. The method of claim 1, wherein the pumping of blood by the pump-conduit assembly is controlled by a control system configured to control the pump.

33. The method of claim 32, wherein a parameter of the pump-conduit assembly is controlled by the control system, such parameter including the speed of the pump, the speed of the pump impeller, or the pressure in a conduit.

34. The method of claim 33, wherein a parameter of the pump-conduit assembly is manually adjusted using the control system.

35. The method of claim 33, wherein a parameter of the pump-conduit assembly is automatically adjusted using the control system.

36. The method of claim 33 wherein at least one sensor is located in the pump, a conduit, or in the vascular system of the patient, such sensor measuring at least one of a) the power or current necessary to operate the pump under certain operating conditions, b) a blood speed, c) a rate of blood flow, d) a resistance to blood flow into or out of an accepting vein, e) a blood pressure, pulse pressure, or pulsatility index in the inflow conduit, outflow conduit, or in the accepting vein.

37. The method of claim 1, wherein the control system includes a rechargeable power unit to provide power to the pump of the pump-conduit assembly, including a rechargeable battery.

38. The method of claim 1, wherein the control system receives power from a wall outlet.

39. The method of claim 1, wherein the pump-conduit assembly comprises a first conduit having a first inlet fluidly connected to the donating vein or location and a first outlet fluidly connected to the inlet of the pump, the first conduit for removing venous blood from the donating vein or location.

40. The method of claim 39, wherein the pump-conduit assembly comprises a second conduit having a second outlet to fluidly connect to the accepting vein and a second inlet fluidly connected to the outlet of the pump, the second conduit for moving venous blood into the accepting vein.

41. The method of claim 40, wherein at least one of the first conduit and the second conduit are connected to the blood pump using a connector comprising a barb fitting.

42. The method of claim 40, wherein at least one of the first conduit and the second conduit are connected to the blood pump using a radially-compressive connector.

43. The method of claim 40, wherein at least a portion of the first conduit or the second conduit comprises at least one member selected from polyvinyl chloride, polyethylene, polyurethane, and/or silicone.

44. The method of claim 40, wherein at least a portion of at least one of the first conduit and the second conduit comprises a shape-memory alloy, a self-expanding material, or a radially expansive material.

45. The method of claim 44, wherein the shape-memory alloy is nitinol.

46. The method of claim 45, wherein at least one of the first conduit and the second conduit comprises braided nitinol.

47. The method of claim 45, wherein at least one of the first conduit and the second conduit comprises coiled nitinol.

48. The method of claim 40, wherein at least a portion of the first conduit or the second conduit comprises at least one member selected from PTFE, ePTFE, polyethylene terephthalate, or Dacron.

49. The method of claim 48, wherein the PTFE, ePTFE, polyethylene terephthalate, or Dacron segment is less than 5 cm in length.

50. The method of claim 40, wherein the distal portion or tip of the second conduit is inserted into the lumen of the accepting vein.

51. The method of claim 50, wherein the distal portion or tip of the second conduit that is inserted into the lumen of the accepting vein comprises walls with are self-expanding or radially expansive.

52. The method of claim 51, wherein the distal portion of the second conduit that is inserted into the lumen of the accepting veins comprises nitinol.

53. The method of claim 40, wherein at least a portion of the first conduit or the second conduit comprises one or more of an antimicrobial coating.

54. The method of claim 40, wherein at least a portion of the lumen of the first conduit or the second conduit comprises an antithrombotic coating.

55. The method of claim 50, wherein the antithrombotic coating comprises heparin.

56. The method of claim 40, wherein at least a portion of the lumen of the first conduit or the second conduit comprises a lubricious coating.

57. The method of claim 40, wherein at least one of the first conduit and the second conduit comprises a radiopaque marker.

58. The method of claim 40, wherein at least one of the first conduit and the second conduit has an inner diameter between 2 mm and 10 mm.

59. The method of claim 40, wherein at least one of the first conduit or the second conduit has an inner diameter of 4 mm.

60. The method of claim 40, wherein the first and second conduits have a combined length between 2 cm and 220 cm.

61. The method of claim 40, wherein at least a portion of the first conduit or the second conduit is configured for subcutaneous tunneling.

62. The method of claim 40, wherein at least a portion of the first conduit or the second conduit can be trimmed to the desired length and attached to the pump.

63. The method of claim 40, wherein a portion of a first conduit or a second conduit is implanted in a patient and a portion of the conduit is extracorporeal.

64. The method of claim 63, wherein a cuff is attached to at least one of the first conduit and the second conduit after tunneling.

65. The method of claim 40, wherein the tip of the first conduit is placed in the superior vena cava or the right atrium.

66. The method of claim 1, wherein at least a portion of the blood-contacting surface of the pump comprises an antithrombotic coating.

67. The method of claim 66, wherein the antithrombotic coating comprises heparin.

68. The method of claim 1, wherein the pumping venous blood from the donating vein or location into the accepting vein is controlled by a control system.

69. The method of claim 68, wherein the controller comprises a software program that analyzes information from the pump-conduit assembly and automatically adjusts pump parameters, such as pump speed, impeller revolutions per minute, or outflow conduit pressure, to account for changes such as a persistent increased overall diameter and lumen diameter in the accepting vein prior to achieving the desired persistent increased overall diameter and lumen diameter in the accepting vein.

70. The method of claim 68 wherein pump parameters, such as pump speed or impeller revolutions per minute, are adjusted periodically.

71. The method of claim 1, wherein the patient is in need of an arteriovenous fistula or arteriovenous graft for hemodialysis.

72. The method of claim 1, wherein the patient is not eligible for surgery to make an arteriovenous fistula with the accepting vein due to inadequate initial vein diameter.

73. The method of claim 1, wherein the pumping of blood results in an increase in the length of the accepting vein, which persists after pumping has ceased.

\* \* \* \* \*